US011518781B2

(12) United States Patent
Koehnlein

(10) Patent No.: US 11,518,781 B2
(45) Date of Patent: Dec. 6, 2022

(54) PROCESS FOR PROVIDING PEGYLATED PROTEIN COMPOSITION

(71) Applicant: Hoffmann-La Roche Inc., Little Falls, NJ (US)

(72) Inventor: Wolfgang Koehnlein, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 200 days.

(21) Appl. No.: 16/957,160

(22) PCT Filed: Dec. 28, 2018

(86) PCT No.: PCT/EP2018/097124
§ 371 (c)(1),
(2) Date: Jun. 23, 2020

(87) PCT Pub. No.: WO2019/129877
PCT Pub. Date: Jul. 4, 2019

(65) Prior Publication Data
US 2021/0238223 A1 Aug. 5, 2021

(30) Foreign Application Priority Data
Dec. 29, 2017 (EP) .................................. 17211103

(51) Int. Cl.
B01D 15/08 (2006.01)
A61K 47/60 (2017.01)
C07K 1/20 (2006.01)
C07K 14/00 (2006.01)
C07K 14/505 (2006.01)
C07K 16/00 (2006.01)
B01D 15/16 (2006.01)
B01D 15/18 (2006.01)
B01D 15/32 (2006.01)
C12N 9/96 (2006.01)

(52) U.S. Cl.
CPC ............... C07K 1/20 (2013.01); A61K 47/60 (2017.08); B01D 15/166 (2013.01); B01D 15/1871 (2013.01); B01D 15/327 (2013.01); C07K 14/505 (2013.01); C12N 9/96 (2013.01)

(58) Field of Classification Search
None
See application file for complete search history.

(56) References Cited

U.S. PATENT DOCUMENTS

| 5,378,808 A * | 1/1995 | D'Andrea | C07K 16/22 435/69.1 |
|---|---|---|---|
| 5,641,670 A | 6/1997 | Treco et al. | |
| 5,733,761 A | 3/1998 | Treco et al. | |
| 5,886,155 A | 3/1999 | Armah et al. | |
| 5,932,462 A | 8/1999 | Harris et al. | |
| 6,583,272 B1 | 6/2003 | Bailon | |
| 8,969,532 B2 | 3/2015 | DeFrees et al. | |
| 2008/0253992 A1* | 10/2008 | DeFrees | A61P 7/06 435/68.1 |
| 2018/0327446 A1* | 11/2018 | Fong | C07K 1/165 |

FOREIGN PATENT DOCUMENTS

| CN | 102453087 A | 5/2012 |
|---|---|---|
| CN | 104513306 B | 8/2016 |
| EP | 0473084 B1 | 11/1995 |
| EP | 1064951 B1 | 8/2007 |
| JP | 2001-112469 A | 4/2001 |
| WO | 9011354 A1 | 10/1990 |
| WO | 9106667 A1 | 5/1991 |
| WO | 9109955 A1 | 7/1991 |
| WO | 9309222 A2 | 5/1993 |
| WO | 9401451 A2 | 1/1994 |
| WO | 9412650 A2 | 6/1994 |
| WO | 9531560 A1 | 11/1995 |
| WO | 0044785 A1 | 8/2000 |
| WO | 2004056852 A2 | 7/2004 |
| WO | 2006024953 A2 | 3/2006 |
| WO | 2007010552 A2 | 1/2007 |
| WO | 2008057683 A2 | 5/2008 |
| WO | 2009010270 A2 | 1/2009 |
| WO | 2011064247 A1 | 6/2011 |
| WO | 2012035037 A1 | 3/2012 |
| WO | 2013138730 A1 | 9/2013 |

OTHER PUBLICATIONS

US 5,733,746 A, 03/1998, Treco et al. (withdrawn)
The English translation of the Japanese Office Action, dated Aug. 11, 2021, in the related Japanese Appl. No. 2020-536096.
The English translation of the Japanese Office Action, dated Sep. 13, 2021, in the related Japanese Appl. No. 2020-536134.
The English translation of the Japanese Office Action, dated Aug. 25, 2021, in the related Japanese Appl. No. 2020-536191.
Snider et al., "Characterization of the heterogeneity of polyethylene glycol-modified superoxide dismutase by chromatographic and electrophoretic techniques," Journal of Chromatography, vol. 599, Issues 1-2, May 22, 1992, pp. 141-155.
European Search Report on Priority Application EP 17211122.1 dated Jun. 12, 2018.
European Search Report on Priority Application EP 17211124.7 dated Jun. 12, 2018.
European Search Report on Priority Application EP 17211103.1 dated Jun. 13, 2018.

(Continued)

Primary Examiner — Elizabeth C. Kemmerer
Assistant Examiner — Regina M DeBerry

(57) ABSTRACT

A process for providing a mono-PEGylated protein composition is provided. The process is particularly suitable for providing mono-PEGylated erythropoietin composition. The process comprises subjecting a mixture comprising non-PEGylated, mono-PEGylated and oligo-PEGylated to a hydrophobic interaction chromatography process.

17 Claims, 7 Drawing Sheets

Specification includes a Sequence Listing.

(56) References Cited

OTHER PUBLICATIONS

International Search Report and Written Opinion on PCT/EP2018/097124 dated Apr. 11, 2019.
International Search Report and Written Opinion on PCT/EP2018/097125 dated Apr. 11, 2019.
International Search Report and Written Opinion on PCT/EP2018/097122 dated Jun. 14, 2019.
Delgado, C., et al., "The Uses and Properties of PEG-Linked Proteins," Crit. Rev. Ther. Drug Carrier 30 Systems 9 (1992) 249-304).
Francis, G.E., et al., "PEGylation of cytokines and other therapeutic proteins and peptides: the importance of biological optimisation of coupling techniques," Int. J. Hematol. 68 (1998) 1-18.
Huang., et al., "Purifying monosubstitutive polyethylene glycol erythropoietin (PEG-EP0) from mixture (EP0, PEG, mono-substitutive PEG-EP0, disubstitutive PEG-EP0 and polysubstitutive PEG-EP0, comprises purifying the mixture", WPI / 2017 Clarivate Analytics, vol. 2012, No. 41, May 16, 2012.
Ingold et al, "A reactive continuous chromatographic process for protein PEGylation," React. Chem. Eng., 2016, 1,218.
Lu, Y., et al., "Pegylated peptides III. Solid-phase synthesis with pegylating reagents of varying molecular weight: synthesis of multiply pegylated peptides," Reactive Polymers 22 (1994) 221-229.
Mayolo-Deloisa K, et al., "PEGylated protein separation using different hydrophobic interaction supports: Conventional and monolithic supports," Biotechnology Progress (2016), 32(3), 702-707.
Morpurgo, M., et al., "Preparation and Characterization of Poly-(ethylene glycol) Vinyl Sulfone," J. Bioconjug. Chem. 7 (1996) 363-368.
Muller, E, et al., "Solubility and binding properties of PEGylated lysozyme derivatives with increasing molecular weight on hydrophobic-interaction chromatographic resins," J. Chromatography, (2010), 217(28), 4696-4703.
Pfister et al, "Model-based development of an on-column PEGylation process," Reac React. Chem. Eng., 2016, 1,204.
Pfister et al. "Integrated Process for High Conversion and High Yield Protein PEGylation," Biotechnology and Bioengineering, 2016, 113, 1711-1718.
Shang, X et al., "Purification and analysis of mono-PEGylated HSA by hydrophobic interaction membrane chromatography," J. Separation Science (2013), 36(23), 3673-3681.
Veronese, F.M., "Peptide and protein PEGylation: a review of problems and solutions," Biomaterials 22 (2001) 405-417.
Vickova, "Pharmaceutical applications of isoelectric focusing on microchip with imaged UV detection," J. Chromatography A (2008) 145-152.
Yu, D et al., "Fractionation of different PEGylated forms of a protein by chromatography using environment-responsive membranes," J. Chromatography, (2010), 1217(35) 5595-5601.
Bristow, "III. Collaborative Study for the Establishment of a Biological Reference Preparation for Erythropoietin," Pharmeuropa Spec. Issue Biologicals BRP Erythropoietin Bio 97-2 (1997) 31-48.
Fee et al., "PEG-Proteins: Reaction Engineering and Separation Issues," Chemical Engineering Science, 2016, 61, pp. 924-939.
Arthur M. Felix, "Chapter 16 Site-Specific Poly(ethylene glycol)ylation of Peptides," ACS Symposium Series, 680: pp. 218-238, (1997).
"Hydrophobic Interaction and Reversed Phase Chromatography, Principles and Methods," GE Handbook, 2006, pp. 1-164.

\* cited by examiner

PROCESS FOR PROVIDING PEGYLATED PROTEIN COMPOSITION

CROSS-REFERENCE TO RELATED APPLICATIONS

This application is a National Stage Application of PCT/EP2018/097124 filed Dec. 28, 2018, which claims priority from European Patent Application No. 17211103.1, filed on Dec. 29, 2017. The priority of said PCT and European Patent Application are claimed. Each of prior mentioned applications is hereby incorporated by reference herein in its entirety.

FIELD OF THE INVENTION

The present invention relates to processes for providing PEGylated protein compositions, particularly processes for providing mono-PEGylated protein compositions. In particular the present invention relates to processes for providing mono-PEGylated erythropoietin (EPO) compositions.

BACKGROUND

PEGylation, or pegylation, of proteins refers to the addition of one or more PEG (polyethylene glycol) groups to a protein. PEGylation is particularly useful for therapeutic proteins, for example because it increases in vivo circulation half-life. However, PEGylation may also reduce the biological activity of therapeutic proteins, thereby reducing their effectiveness. There is therefore a balance to be struck between increased circulation time and reduced therapeutic efficacy.

For certain therapeutic proteins, mono-PEGylation is particularly desirable because it provides improved stability without significantly compromising therapeutic efficacy. Mono-PEGylated therapeutic proteins include Mircera®, PegIntron® and Pegasys®. Micera® is a mono-PEGylated form of erythropoietin (EPO) and is used to treat anaemia.

PEGylation reactions tend to produce mixtures comprising non-PEGylated protein (unreacted protein), mono-PEGylated protein, and oligo-PEGylated protein. Reaction conditions that favour a high degree of PEGylation (such as long reaction times, high PEG/protein molar ratio) tend to produce mixture with a high proportion of oligo-PEGylated protein, which results in low yields when mono-PEGylated protein is the desired product. Reaction conditions that favour a low degree of PEGylation (such as short reaction times, low PEG/protein molar ratio) tend to produce mixtures with a high proportion of unreacted (non-PEGylated) protein, which also results in low yields when mono-PEGylated protein is the desired product.

Therapeutic proteins are often expensive to manufacture and therefore processes that provide good yields of mono-PEGylated therapeutic protein (minimal waste of therapeutic protein as unreacted and/or oligo-PEGylated) are economically favourable and therefore are particularly desirable.

Methods of PEGylating a protein of interest while it is bound to an ion exchange chromatography column have been developed in attempts to manipulate the specificity of PEGylation and thereby improve yields of proteins with a desired degree of PEGylation (so-called "on column" methods). Such methods are technically complex and time consuming and consequently have low productivity. Such methods may also consume relatively large amounts of PEGylation reagent, making them economically unfavourable. Various "on column" PEGylation methods are discussed in Pfister (Reac React. Chem. Eng., 2016, 1,204), Ingold (2016) and Fee & Van Alstine (2006).

Methods of providing mono-PEGylated proteins may comprise performing a PEGylation reaction to provide a mixture comprising non-PEGylated protein (unreacted protein), mono-PEGylated protein, and oligo-PEGylated protein, and then performing a purification step to purify the mono-PEGylated protein.

WO 2009/010270 and WO 2012/035037 relate to methods for purifying mono-PEGylated EPO from a mixture comprising non-PEGylated protein, mono-PEGylated protein, and oligo-PEGylated protein. The purification methods involve subjecting the mixture that results from a PEGylation reaction to at least one cation exchange chromatography (CEC) step. The CEC step is performed in bind and elute mode and different elution factions comprise mostly non-PEGylated, mono-PEGylated or oligo-PEGylated EPO. Such CEC methods must be carried out below the isoelectric point of the protein, which in the case of EPO (isoelectric point in the range 4.0 to 5.5) involves CEC at a pH of around 3.0.

Methods for producing mono-PEGylated proteins by performing a PEGylation reaction and then purifying the mono-PEGylated protein from the resultant mixture may involve recycling unreacted (non-PEGylated) protein. These methods involve recovering unreacted protein and adding it to a subsequent PEGylation reaction. Such recycling improves the overall yield of mono-PEGylated protein.

Pfister (Biotech and Bioeng, 2016) describes a process in which a PEGylation reaction is performed followed by purification of mono-PEGylated protein from a mixture comprising unreacted (non-PEGylated), mono-PEGylated, and oligo-PEGylated protein. In the process unreacted protein is recovered and used in a subsequent PEGylation reaction. The purification process comprises cation exchange chromatography (CEC) in bind and elute mode, wherein unreacted protein, mono-PEGylated protein and oligo-PEGylated protein are separated in sequential elution. Unreacted protein is eluted last, using a high salt elution buffer. The elution of the unreacted protein in the final stage of CEC delays the recycling of unreacted protein, since it is processed by diafiltration before recycling, thereby reducing the overall productivity of the process.

The present invention has been devised in light of the above considerations.

SUMMARY OF THE INVENTION

The present invention relates to processes for providing mono-PEGylated protein compositions. The processes of the invention are particularly suitable for providing mono-PEGylated EPO compositions. Advantages of the process described herein include high yield and productivity and high purity of mono-PEGylated product.

The present invention relates to a process in which a protein mixture comprising non-PEGylated, mono-PEGylated and oligo-PEGylated protein is subjected to a two-stage hydrophobic interaction chromatography (HIC) step. The two-stage HIC step involves applying the protein mixture to two HIC materials under specific conditions ("two-stage HIC conditions"): the first HIC material binds only oligo-PEGylated protein under those conditions, and the second HIC material binds mono-PEGylated protein under those same conditions. That is, the first HIC material binds oligo-PEGylated protein but not non-PEGylated protein or mono-PEGylated protein under the two-stage HIC conditions. The second HIC material binds mono-PEGylated protein under the two-stage HIC conditions, and is capable of binding oligo-PEGylated protein under the two-stage HIC conditions but in the processes disclosed herein substantially all of the oligo-PEGylated protein may have already been removed by the first HIC material, so in carrying out the invention the second HIC material does not necessarily bind oligo-PEGylated protein, or does not bind significant amounts of oligo-PEGylated protein.

In particular, the present invention provides a process for producing a mono-PEGylated protein composition comprising at least about 90% mono-PEGylated protein, the process comprising: a) providing a protein mixture comprising non-PEGylated protein, mono-PEGylated protein and oligo-PEGylated protein; b) subjecting the protein mixture to a two-stage hydrophobic interaction chromatography (HIC) step, comprising: applying the protein mixture to a first HIC material to provide a first HIC flow-through solution; and applying the first HIC flow-through solution to a second HIC material to provide a second HIC flow-through solution, wherein the second HIC material is different from the first HIC material; and wherein the two-stage HIC step is performed under two-stage HIC conditions, which two-stage HIC conditions are suitable for binding oligo-PEGylated protein to the first HIC material and binding mono-PEGylated protein to the second HIC material; and c) eluting the mono-PEGylated protein from the second HIC material to provide a second HIC eluate, wherein the second HIC eluate provides the mono-PEGylated protein composition.

The "second HIC eluate" may also be referred to as a "second HIC material eluate", because it is the eluate from the second HIC material in the two-stage HIC step.

In the processes disclosed herein the mono-PEGylated protein composition may contain a relatively high proportion of mono-PEGylated protein. For example, the protein composition may comprise at least about 95%, 98%, 99%, or 99.9% mono-PEGylated protein.

The protein may be erythropoietin (EPO). The protein may be a hormone. The protein may be a hormone, a cytokine, an enzyme or an antibody.

Mono-PEGylated proteins may be desirable because they provide a balance between increased half-life and comparable biological activity relative to non-PEGylated and oligo-PEGylated versions of the protein. However PEGylation reactions tend to produce mixtures comprising non-PEGylated protein (unreacted protein), mono-PEGylated protein, and oligo-PEGylated protein. Proteins, especially therapeutic proteins, are often expensive to manufacture and therefore processes that provide good yields of mono-PEGylated therapeutic protein particularly desirable. Processes that provide good yields of mono-PEGylated EPO (Mircera®) are particularly desirable.

The processes disclosed herein are advantageous because they may enable rapid recovery of non-PEGylated protein (unreacted protein) for subsequent processing and recycling in a subsequent PEGylation reaction. The processes disclosed herein may enable relatively high yield because non-PEGylated EPO may be recovered and recycled, thus a greater proportion of the starting protein becomes mono-PEGylated.

The processes disclosed herein are advantageous relative to processes that recycle non-PEGylated protein in which the non-PEGylated protein is recovered after the mono-PEGylated protein. This is because the processes disclosed herein enable recovery of the non-PEGylated protein at an early stage of the process, before recovery of the mono-PEGylated protein, which means the non-PEGylated protein may be processed and recycled in parallel with later stages of the process. This increases the overall productivity of processes that involve a step of recycling non-PEGylated protein. The processes disclosed herein are advantageous because they involve HIC, which can be performed at a pH close to physiological pH. This may improve the stability of the protein. The processes of the invention are particularly suitable for producing mono-PEGylated EPO compositions. This is advantageous over processes involving cation exchange chromatography (CEC) for producing mono-PEGylated EPO which are generally performed at a pH of 3.0 or lower. Acidic conditions of about pH 3.0 or lower may have adverse effects on EPO quality, such adverse effects are reduced in the processes of the present invention, which do not require CEC and thus do not require the low pH conditions necessary for CEC-based purification of EPO.

Furthermore, acid forms (acidic variants) of EPO may have high therapeutic activity, making them particularly useful. However, recovery of mono-PEGylated acidic forms of EPO by CEC may be poor because their elution conditions in CEC are similar to those of di-PEGylated non-acidic forms of EPO. Acidic conditions result in the oxidation of the side chains of amino acids in a protein molecule. As CEC separates protein molecules according to their charge, basic variants of a species will elute later than acidic variants. For this reason, the CEC elution profile of di-pegylated non-acidic forms of EPO tends to overlap with mono-PEGylated acidic forms of EPO. The poor recovery of these useful mono-PEGylated acidic EPO forms by CEC is reduced in the processes disclosed herein, which do not rely on CEC to separate mono-PEGylated from oligo-PEGylated EPO.

Purification of proteins by HIC is based on hydrophobicity of the protein rather than charge. The processes disclosed herein may be advantageous because they are relatively unaffected by acidic forms or by glycosylation variants that affect protein charge. Because PEGylation may greatly affect the hydrophobicity of a protein, the processes disclosed herein are particularly useful for providing mono-PEGylated protein compositions.

The advantages associated with the invention to provide mono-PEGylated EPO may apply to other proteins, particularly other therapeutic proteins. That is, avoidance of low pH conditions and recovery of acidic variants may render the invention useful for providing mono-PEGylated proteins other than mono-PEGylated EPO.

The processes disclosed herein are for producing a mono-PEGylated protein composition using a protein mixture that comprises non-PEGylated, mono-PEGylated and oligo-PEGylated protein. In the processes disclosed herein two HIC materials are used in series in a two-stage HIC step. The two HIC materials are different from each other and are selected such that, under the conditions used for the two-stage HIC step, the first HIC material binds oligo-PEGylated protein (but not mono-PEGylated protein), the second HIC material binds mono-PEGylated protein, and neither the first nor the second HIC material binds non-PEGylated protein. Thus as the protein mixture passes over the first HIC material the oligo-PEGylated protein is sequestered (and can be eluted later) and as it passes over the second HIC material the mono-PEGylated protein is sequestered (for elution later). The non-PEGylated protein passes over both the first and second HIC materials and can be removed in the flow-through from the two-stage HIC step, and may be subsequently recycled. Thus the non-PEGylated (unreacted) protein is recovered very quickly from the protein mixture for recycling. The mono-PEGylated protein is then eluted from the second HIC material, to provide a mono-PEGylated protein composition.

The same HIC conditions are used for HIC involving both the first and second HIC materials (these may be referred to as "two-stage HIC conditions"). This means that there is no need to change buffers between the first and second stages of the HIC step. The two-stage HIC conditions may be isocratic. There is no need to condition or alter the composition of the flow-through solution from the first HIC material before applying it to the second HIC material. The flow-through solution from the first HIC material can be directly applied to the second HIC material. This saves time-consuming adjustment of HIC conditions thereby improving efficiency and productivity. This means that the first HIC material and second HIC material may be connected directly in series, such that the flow-through solution from the first HIC step can be quickly and efficiently delivered to the second HIC material. The overall process is relatively fast, cheap and efficient.

The two-stage HIC step uses two different HIC materials. The first HIC material is used to capture (i.e. sequester, bind, remove) only or primarily the oligo-PEGylated protein. The second HIC material is used to capture only or primarily the mono-PEGylated protein. An advantage of this is that the binding capacity of the first HIC material is only or primarily used for binding the undesired oligo-PEGylated protein (a contaminant in this context), and the second HIC material is only or primarily used for binding the desired mono-PEGylated protein (the product in this context). This means that the process has relatively high productivity relative to the amount of HIC material employed. Because most or all of the available binding capacity is used for binding either the contaminant or the product, the load can be relatively high. That is, the amount of protein mixture that is applied to the HIC materials can be relatively high. This means that the overall process has relatively high productivity, because it can produce large amounts of mono-PEGylated protein composition within a time period, or per cycle.

The process may be carried out using buffer solutions that comprise a buffer such as HEPES. The buffer solutions may be at physiological pH, for example pH 7.0-8.0 or around pH 7.5. The buffer solutions may contain varying amounts of salt such as $Na_2SO_4$. In general equilibration buffers and wash buffers contain relatively high salt concentrations (e.g. about 400-600 mM or about 500 mM), whereas elution buffers contain relatively low salt concentrations (e.g. about 0-300 mM).

The HIC materials may comprise phenyl ligands. The first HIC material may be Phenyl Sepharose HP (for example, HiTrap Phenyl HP available from GE Healthcare). The second HIC material may be Toyopearl Phenyl 650M (Tosoh Bioscience LLC). In particular if the mono-PEGylated protein is mono-PEGylated EPO the first HIC material may be Phenyl Sepharose High HP and the second HIC material may be Toyopearl Phenyl 650M.

SUMMARY OF THE FIGURES

Embodiments and experiments illustrating the principles of the invention will now be discussed with reference to the accompanying figures.

FIG. 4. Scheme showing embodiment of process as disclosed herein.

DETAILED DESCRIPTION OF THE INVENTION

Figure 1:
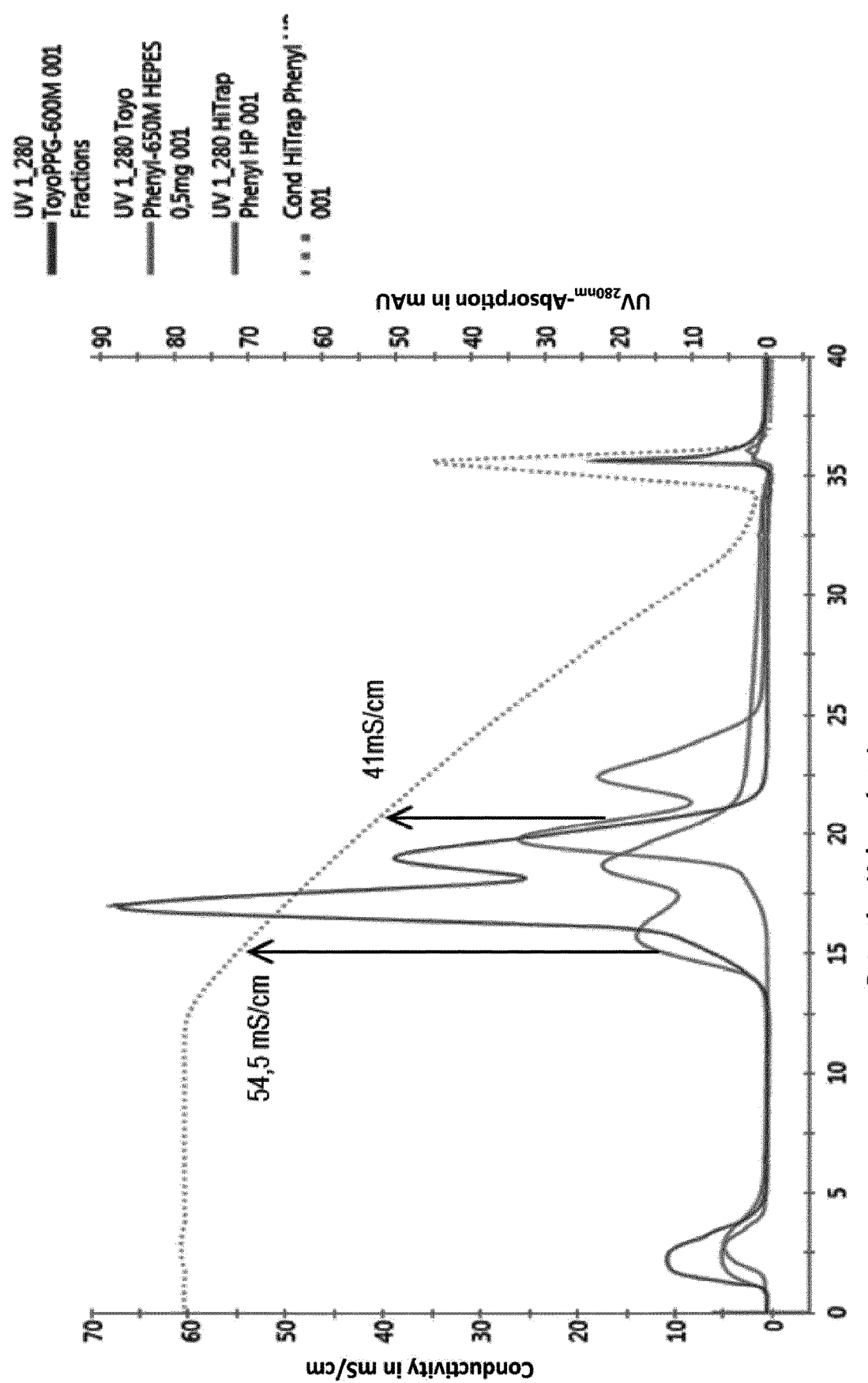
FIG. 1. Comparative chromatogram. Comparison of the UV chromatograms of columns of the HIC materials Toyopearl Phenyl 650M, Phenyl Sepharose HP, and Toyopearl PPG 600M. The conductivity of fractions from the Phenyl Sepharose HP column is shown by the dotted line. The columns are equilibrated at 60 mS/cm. The first peak for each column is non-PEGylated EPO, which is in the flow-through solution from the column. The mono-PEGylated EPO and oligo-PEGylated EPO are eluted by a falling salt gradient, which decreases the conductivity to about 1 mS/cm (this is achieved by increasing the proportion of low salt buffer B from 0% to 100%, which decreases the $Na_2SO_4$ concentration from about 500 mM to about 0 mM). The trace with the highest peaks is Toyopearl PPG 600M, the trace with the earliest mono-PEGylated EPO peak is Phenyl Sepharose HP, and the remaining trace is Toyopearl Phenyl 650M.

Aspects and embodiments of the present invention will now be discussed with reference to the accompanying figures. Further aspects and embodiments will be apparent to those skilled in the art. All documents mentioned in this text are incorporated herein by reference.

The present invention relates to processes for providing mono-PEGylated protein compositions. The present invention relates to processes for providing a protein composition comprising at least 90% mono-PEGylated protein. In particular, the present invention provides processes for providing an EPO composition comprising at least 90% mono-PEGylated EPO.

Mono-PEGylated Protein Compositions

In the present context, a mono-PEGylated protein composition is a composition comprising a protein, wherein a relatively high proportion of the protein present in the composition is present as mono-PEGylated protein. A mono-PEGylated protein composition may comprise at least about 90%, 95%, 96%, 97%, 98%, 99%, 99.5%, 99.9% or 99.99% mono-PEGylated protein A protein composition comprising at least x % mono-PEGylated protein refers to a protein composition in which at least x % of the protein present in that composition is mono-PEGylated. For example, a protein composition comprising at least 99% mono-PEGylated protein is a protein composition in which at least 99% of that protein present in the composition is mono-PEGylated. Protein compositions produced by the processes of the invention may comprise at least about 90%, at least about 95%, 96%, 97%, 98%, 99%, 99.5%, 99.9% or 99.99% mono-PEGylated protein.

In particular, in the present context, a mono-PEGylated EPO composition is a composition comprising EPO, wherein a relatively high proportion of the EPO present in the composition is present as mono-PEGylated EPO. An EPO composition comprising at least "x %" mono-PEGylated EPO refers to an EPO composition in which at least "x %" of the EPO present in that composition is mono-PEGylated. For example, an EPO composition comprising at least 99% mono-PEGylated EPO is an EPO composition in which at least 99% of the EPO present in the composition is mono-PEGylated. EPO compositions produced by the processes of the invention may comprise at least about 90%, at least about 95%, 96%, 97%, 98%, 99%, 99.5%, 99.9%, or 99.99% mono-PEGylated EPO. EPO compositions produced by the processes of the invention may comprise at least about 98% mono-PEGylated EPO. EPO compositions produced by the processes of the invention may comprise at least about 99% mono-PEGylated EPO.

Methods for the determination of purity are known to those of skill in the art. Purity of a non-PEGylated, mono-PEGylated or oligo-PEGylated protein may be determined by any suitable method of analysis (e.g. band intensity on gel, ELISA, HPLC and the like). Determination of purity may involve using a standard curve generated using a reference material of known purity. Purity may also be determined on a weight-by-weight basis. The purity of a non-PEGylated or PEGylated protein expressed herein in percentage terms (%) may be determined for example using relative "area under the curve" values, which can typically be obtained for peaks in a chromatogram, such as an HPLC chromatogram. Methods of determining purity include RP-HPLC and size exclusion chromatography (SEC).

Hydrophobic Interaction Chromatography

Hydrophobic interaction chromatography (HIC) separates molecules on the basis of differences in their surface hydrophobicity. It can be used to separate protein molecules. In HIC a mixture including a protein of interest may be passed over an HIC material. The interaction between proteins and a HIC material is altered by the presence of certain salts. Increasing the salt concentration increases the interaction and reducing the salt concentration reduces the interaction. For selective elution, the salt concentration may be lowered and the components of the mixture elute in order of hydrophobicity, the most hydrophobic components eluting last. In the present context, this means that non-PEGylated proteins leave the HIC material first, and mono-PEGylated proteins are eluted before oligo-PEGylated proteins.

A chromatography "material" in the present context, such as a HIC material, refers to the stationary phase or solid phase. This may also be referred to as a resin or matrix or medium. The "material" in this context provides a matrix to which a component of a mixture, such as protein of interest, may bind. The material may be or may comprise a column, for example an expanded bed or packed bed column. The material may be in the form of discrete particles or beads. The material may be in the form of a membrane. The material may be in the form of a porous monolithic material. The material may be in the form of a functionalised fibre, fleece, or mesh. The material be in the form of any other solid support able to carry functional groups or exhibiting HIC properties. In the present context the mobile phase flows through the stationary phase and carries the substances to be separated by chromatography with it. The mobile phase is a mixture, such as protein mixture or a flow-through solution. A buffer, such as an elution buffer or wash buffer, is also a mobile phase.

In the present context the term "loading" refers to a step of contacting a mixture or composition onto chromatography material. The chromatography material may be equilibrated before the loading step.

Equilibration involves applying an equilibration buffer to the chromatography material. The pH and ionic strength of the equilibration buffer are selected to ensure that when a protein mixture is loaded onto the chromatography matrix, the desired binding and/or flow through or specific proteins or contaminants is achieved.

The loading conditions may promote binding of unwanted components of the mixture (e.g. contaminants). In this mode, the protein of interest may flow through a matrix of the ion exchange material and be collected. This type of procedure is known as "flow through" mode. The composition that is collected after flowing through a matrix of ion exchange material is the "flow-through" or "flow-through solution". The flow-through solution that comes off the matrix and contains the protein of interest may also be termed "effluent". Unlike "bind and elute" mode, which involves a change in conductivity and/or pH to elute the protein of interest from the column, "flow through" mode is carried out under isocratic conditions.

Elution from a chromatography material, such as a hydrophobic interaction chromatography material, may be achieved by decreasing the ionic strength of a buffer using gradient elution or step elution. Gradient elution, or linear gradient elution, may be used when many components of individual interest are bound to the material and may be eluted differently, and for high resolution separation. Step elution is useful for removing a single component (or removing a specific group of components together) from a chromatography material. Step elution is relatively fast, and consumes less buffer. Step elution may be used to elute a protein of interest from a chromatography material in a relatively concentrated form. The solution that comes off the chromatography material in the elution step and contains the protein of interest may be known as the eluant or eluate.

HIC Materials

HIC materials may comprise a basal matrix that has been functionalised with a hydrophobic ligand. Hydrophobic ligands on HIC materials may interact with hydrophobic surfaces of proteins. The ligand and the degree of substitution (high or low substitution "sub") on a HIC material may contribute to its final hydrophobicity and thereby to its selectivity. The ligand may contain alkyl or aryl groups. The hydrophobicity of HIC materials increases through the ligand series: ether, polypropyleneglycol (PPG), phenyl, butyl and hexyl. A basal matrix may be Sepharose or a methacrylic polymer.

HIC materials include Toyopearl Ether 650M, Toyopearl Hexyl 650 C, Toyopearl Butyl 650M, Toyopearl PPG 600M, Toyopearl Phenyl 650M (all from Tosoh Bioscience LLC); Phenyl Sepharose FF (hi sub), Phenyl Sepharose FF (low sub), Phenyl Sepharose HP, Butyl Sepharose FF, Butyl-S Sepharose FF, Butyl Sepharose HP, Capto Butyl ImpRes, Capto Phenyl (hi sub).

HIC materials include Toyopearl Phenyl 650S, TSKgel Phenyl SPW, Butyl Sepharose 4 FF, Butyl-S Sepharose FF, Octyl Sepharose 4 FF, Phenyl Sepharose BB, Phenyl Sepharose HP, Phenyl Sepharose 6 FF High Sub, Phenyl Sepharose 6 FF Low Sub, Source I SETH, Source 151 SO, Source 1 SPHE, Phenyl Sepharose BB, Cellufine Butyl, Cellufine Octyl, Cellufine Phenyl, WP HI-Propyl (C3), Macroprep t-Butyl, Macroprep methyl. HIC materials include any other suitable solid support able to carry functional groups or exhibiting HIC properties.

The processes of the invention comprise a two-stage HIC step. The two-stage HIC step involves two different HIC materials. The two different materials may be selected by a screening process.

In the screening process HIC materials are screened for their ability to bind non-PEGylated, mono-PEGylated and oligo-PEGylated versions of a protein in an HIC step involving loading, washing and linear gradient elution of proteins. HIC materials are screened for the ability to separate non-PEGylated, mono-PEGylated and oligo-PEGylated forms of the protein. HIC materials able to separate non-PEGylated, mono-PEGylated and oligo-PEGylated forms of the protein are taken forward as candidates and the remaining HIC materials are excluded from further consideration.

The HIC chromatograms of candidate HIC materials are compared and a pair of HIC materials are selected that exhibit good resolution between peaks for mono-PEGylated protein. FIG. 1 shows HIC chromatograms for three candidate HIC materials. Each HIC material is able to separate non-PEGylated EPO, mono-PEGylated EPO and oligo-PEGylated EPO. In HIC the material is equilibrated with a high salt solution and proteins are eluted by decreasing the salt concentration (in a step or gradient elution) with the most hydrophobic species eluting last. The first peak for each trace is non-PEGylated EPO, which does not bind the HIC materials and leaves in the flow-through solution. The second peak for each trace is mono-PEGylated EPO, and the third peak is oligo-PEGylated EPO.

As can be seen in the comparative chromatograms of FIG. 1, the peaks for mono-PEGylated EPO (the second peak of each trace) show the greatest separation for Phenyl Sepharose HP and Toyopearl Phenyl 650M. This means that this pair of HIC materials is suitable for use in the processes disclosed herein because under the same HIC conditions (same salt concentration) the two materials show different abilities to bind mono-PEGylated EPO. The more hydrophilic HIC material (in this case Phenyl Sepharose HP) is used as the first HIC material, and the more hydrophobic material (in this case Toyopearl Phenyl 650M) is used as the second HIC material.

As can be seen from FIG. 1, at about 60 mS/cm neither Phenyl Sepharose HP nor Toyopearl Phenyl 650M bind to non-PEGylated EPO. This means that a protein mixture can be applied to both HIC materials, the first and then the second, and the non-PEGylated EPO will be recovered in the flow-through solution from the second HIC material.

FIG. 1 also shows that at 54.5 mS/cm Phenyl Sepharose HP (the first HIC material) does not bind mono-PEGylated EPO whereas Toyopearl Phenyl 650M (the second HIC material) does bind mono-PEGylated EPO. This means that a protein mixture can be applied to the first HIC material and then the second HIC material under the same conditions and the mono-PEGylated EPO will only bind to the second HIC material. FIG. 1 also shows that 54.5 mS/cm Phenyl Sepharose HP (the first HIC material) still binds oligo-PEGylated EPO, and therefore the first HIC material will sequester all or most of the oligo-PEGylated EPO before it reaches the second HIC material.

FIG. 1 also shows that at about 41 mS/cm Toyopearl Phenyl 650M (the second HIC material) no longer binds mono-PEGylated EPO, and therefore the mono-PEGylated EPO can be eluted from the second HIC material at around this conductivity.

The results shown in FIG. 1 demonstrate that the processes disclosed herein may be performed using Phenyl Sepharose HP as the first HIC material and Toyopearl Phenyl 650M as the second HIC material.

The conductivity values (salt concentrations) suitable for the different buffers during the step of two-stage HIC and the step of elution of the second HIC material can be determined from the type of comparative chromatograph study shown in FIG. 1.

The screening process described herein can be repeated for other types of HIC materials in order to find further pairs of HIC materials suitable for performing the processes of the present invention, either on EPO mixtures comprising non-PEGylated, mono-PEGylated and oligo-PEGylated EPO, or on other protein mixtures comprising non-PEGylated, mono-PEGylated and oligo-PEGylated EPO.

The skilled person familiar with HIC techniques is able to perform the screening process described herein to identify further pairs of HIC materials and suitable two-stage HIC conditions for providing mono-PEGylated protein compositions. This is because it is well established in the HIC field that selection of HIC materials and sample components are usually made empirically, because the hydrophobic behaviour of a protein is difficult to predict. It is therefore common practice in HIC to determine the most suitable HIC material and salt type and concentrations to be used on a case by case basis.

Performance of HIC materials (selectivity, resolution and binding capacity) is known to be influenced by many parameters: protein properties, ligand type, degree of ligand substitution, concentration and type of salt used during protein application, and presence of detergents. To a lesser degree temperature, pH and type of base matrix (e.g. Sepharose) may have some effect. The most important parameters for determining HIC material performance for a specific protein are ligand type and degree of ligand substitution (the hydrophobicity of the HIC material—the stationary phase) and the type and concentration of salt (the conductivity of the load and buffer solutions—the mobile phase).

The most common ligands used in HIC materials are phenyl, butyl-S, butyl, octyl, ether and isopropyl.

A higher degree of ligand substitution (higher ligand density) provides a more hydrophobic HIC material. For example a HIC material with a name including "hi sub" will be more hydrophobic than the corresponding "low sub" HIC material.

The ability of a particular salt to promote hydrophobic interaction between a protein and a HIC material depends on the ionic species present and their concentration. Several types of salts may be tested when screening the suitability of a particular HIC material for use in the processes disclosed herein. As the concentration of salt is increased the amount of protein bound to the HIC material increases up to the precipitation point for the protein. Commonly used salts in HIC include $(NH_4)_2SO_4$, $Na_2SO_4$, NaCl, KCl and $CH_3COONH_4$. Salts may include any of the following anions in combination with any of the following cations. Anions, in order of decreasing precipitation effect, are $PO_4^{3-}$, $SO_4^{2-}$, $CH_3COO^-$, $Cl^-$, $Br^-$, $NO_3^-$, $ClO_4^-$, $SCN^-$. Cations, in order of increasing chaotropic effect are $NH_4^+$, $Rb^+$, $K^+$, $Na^+$, $Cs^+$, $Li^{2+}$, $Mg^{2+}$, $Ca^{2+}$, $Ba^{2+}$.

The skilled person is able to vary the type and degree of substitution of ligand on the HIC material, and the type and concentration of the salt, in order to provide or screen for a particular protein profile. For example, if the protein species of interest does not bind under high salt conditions, then a more hydrophobic medium can be used. If a protein species that is wanted to remain in the flow-through solution (such as non-PEGylated protein) is binds HIC material under high salt conditions at the start of the process, the salt concentration in the equilibration buffer can be decreased and/or a less hydrophobic HIC medium can be used.

Both the first HIC material and the second HIC material are capable of resolving non-PEGylated, mono-PEGylated and oligo-PEGylated protein under specific conditions. This feature can be identified using a UV chromatograph of a HIC process under specific conditions. The conditions may comprise applying a protein mixture to the HIC material under high salt conditions and applying a falling gradient of salt concentration to elute the proteins. Suitable HIC materials under high salt conditions (starting conditions) do not bind non-PEGylated protein, such that it can be recovered in the flow-through solution. Suitable HIC materials also resolve mono-PEGylated and oligo-PEGylated proteins during the elution gradient. Particularly suitable HIC materials are those showing relatively narrow, relatively high, and/or relatively symmetrical elution peaks for each of the mono-PEGylated and oligo-PEGylated species.

The processes disclosed herein comprise a two-stage HIC step that uses two different HIC materials: a first HIC material and a second HIC material. The first HIC material and second HIC material may be referred to as a pair of HIC materials.

A suitable pair of HIC materials for use in the processes disclosed herein may be identified by overlaying the HIC chromatograms for a specific protein mixture under specific HIC conditions, to provide a comparative HIC chromatogram. A suitable pair of HIC materials may have good resolution of mono-PEGylated elution peaks. That is the elution peaks of for the mono-PEGylated protein when overlaid in a comparative HIC chromatogram should overlap as little as possible. A suitable pair of HIC materials may be a pair having substantially no overlap of elution peaks for mono-PEGylated protein. That is, there is substantially no overlap of elution peak for mono-PEGylated protein of the two HIC materials. A suitable pair of HIC materials may be a pair having little overlap of elution peaks for mono-PEGylated protein. Such pairs of HIC materials may be referred to as having well-resolved peaks for mono-PEGylated product.

Resolution ($R_s$) between two elution peaks may be defined as the distance between peak maxima compared with the average base width of the two peaks (see *Hydrophobic Interaction and Reversed Phase Chromatography, Principles and Methods*, GE Handbook, 2006). Elution volumes and peak widths are measured with the same units to give a dimensionless resolution value $R_s$ which provides a measure of the relative separation between two peaks.

Resolution, $R_s$, a measure of how well two peaks are separated, can be expressed as:

$$Rs = \frac{t_{r2} - t_{r1}}{(W_{b2} + W_{b1})/2}$$

Where $t_{r1}$ and $W_{b1}$ are the retention time and baseline width respectively for the first eluting peak, and $t_{r2}$ and $W_{b2}$ are the retention time and baseline width respectively for the second eluting peak.

In the processes disclosed herein a HIC material may resolve mono-PEGylated and oligo-PEGylated proteins under specific conditions to provide a HIC chromatogram in which the respective elution peaks have a resolution ($R_s$) of at least 0.5, 0.8, 1.0, 1.2, or 1.5.

A HIC material for use in the processes disclosed herein may show well-resolved elution peaks for mono-PEGylated and oligo-PEGylated protein.

A HIC material for use as a second HIC material in the processes disclosed herein may show a mono-PEGylated protein elution peak having a composition of at least 95%, 98%, 99%, 99.5% or 99.9% or about 100% mono-PEGylated protein. For example in the experiments described below Toyopearl Phenyl 650M was found to provide HIC fraction of mono-PEGylated EPO comprising at about 100% mono-PEGylated EPO (Tables 3 and 6).

In the processes disclosed herein a pair of HIC materials may provide a comparative HIC chromatogram in which the peaks for mono-PEGylated protein for each respective HIC material have a resolution ($R_s$) of at least 0.8, 1.0, 1.2, or 1.5. Such a pair of HIC materials may be referred to as having well-resolved peaks for mono-PEGylated product. A comparative HIC chromatogram is an overlay of chromatogram traces for two or more different HIC materials under the same HIC conditions. A comparative HIC chromatogram allows the elution peaks for different HIC materials under the same conditions to be compared.

Figure 4A:
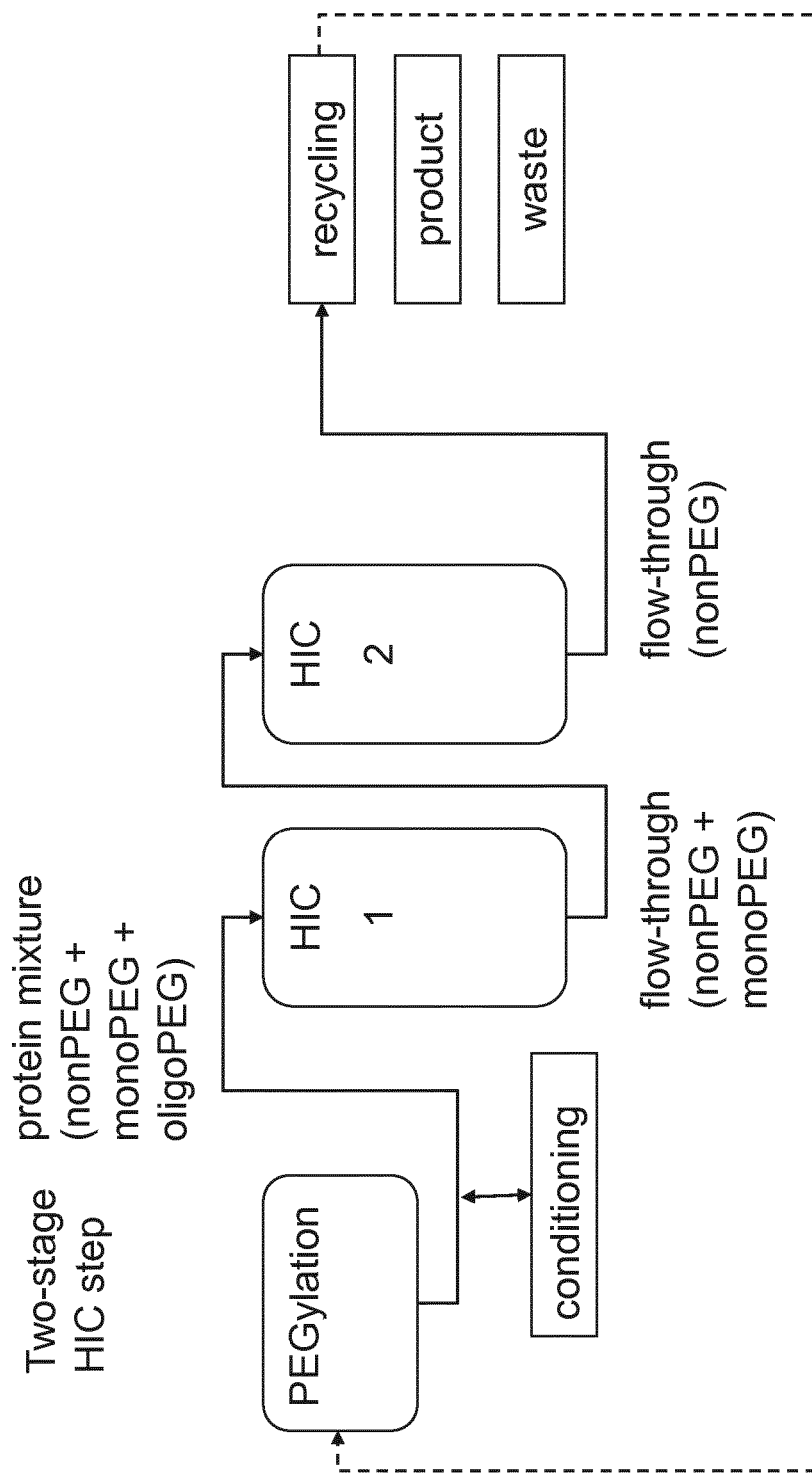
FIG. 4A shows columns of the first HIC material (HIC 1) and the second HIC material (HIC 2) connected in series. A PEGylation reaction vessel provides a protein mixture that is applied to the first HIC material. There may be an intervening conditioning step to prepare the protein mixture for loading onto the first HIC material (conditioning). The two-stage HIC step involves applying the protein mixture to the first HIC material to obtain a first HIC flow-through solution, which is applied to the second HIC material to obtain a second HIC flow-through solution. The second-HIC flow-through solution contains a relatively high proportion of non-PEGylated protein, which may be recycled in a subsequent PEGylation reaction.
Figure 4B:
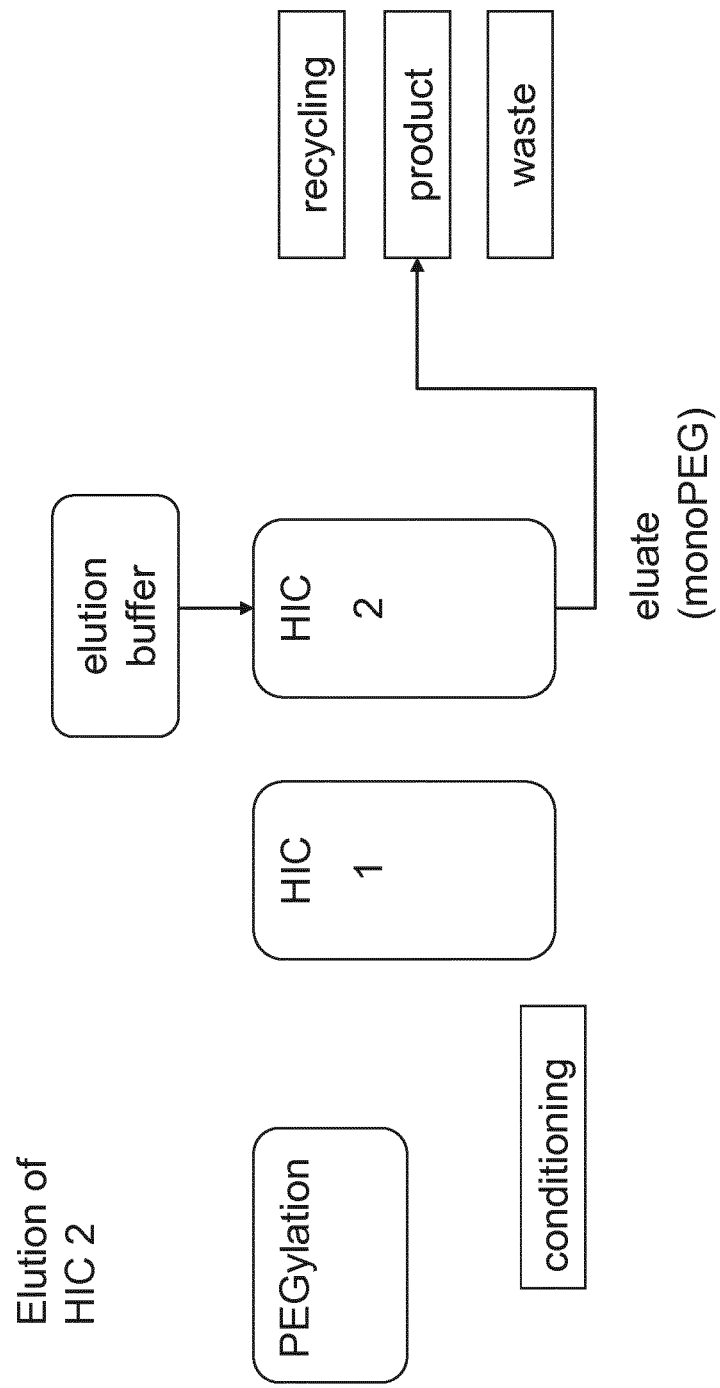
FIG. 4B shows elution of the second HIC material with an elution buffer, this elution recovers mono-PEGylated protein from the second HIC material. The eluate from the second HIC material provides a mono-PEGylated protein composition (the desired product).
Figure 4C:
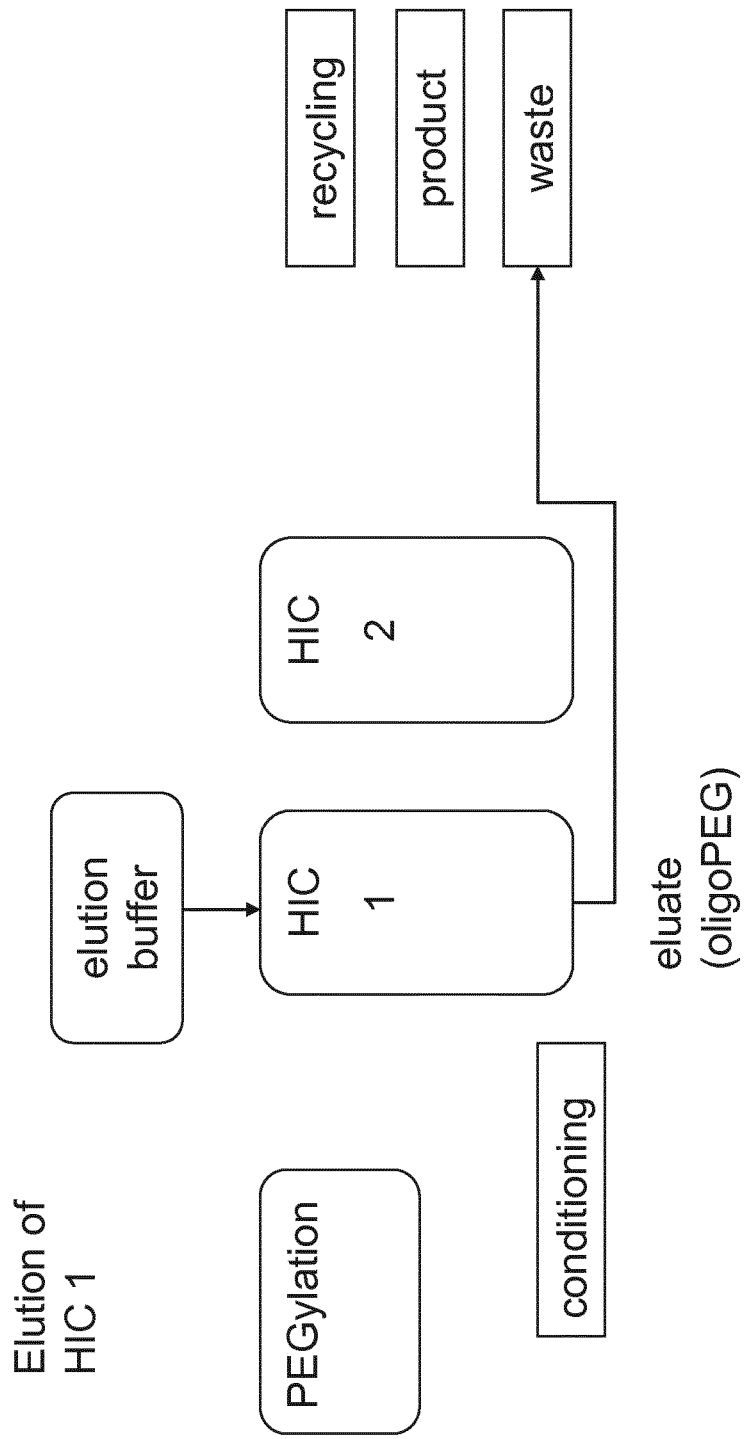
FIG. 4C shows elution of the first HIC material with an elution buffer, this elution removes oligo-PEGylated protein from the first HIC material.

A pair of HIC materials may provide a comparative HIC chromatogram in which the respective elution peaks for mono-PEGylated and/or oligo-PEGylated protein have maxima separated by retention volumes of at least 3 mL when using the chromatography design in Example 1 (FIG. 4), or that have maxima with retention volume, or wherein the elution peak of the second HIC material is more than 10%, 15% or 20% greater in terms of retention volume than the corresponding elution peak of the first HIC material.

In a comparative HIC chromatogram for a suitable pair of HIC materials, the HIC material for which the mono-PEGylated protein elution peak is earlier (retention volume is lower) may be used as the first HIC material. The first HIC material may be described as more hydrophilic (or less hydrophobic) than the second HIC material.

Processes for Producing Mono-PEGylated Protein Compositions

The present invention provides a process for producing a mono-PEGylated protein composition. The present invention provides a process for purifying mono-PEGylated protein from a mixture comprising non-PEGylated protein, mono-PEGylated protein and oligo-PEGylated protein.

The present invention provides a process for producing a mono-PEGylated protein composition comprising at least about 90% mono-PEGylated protein, the process comprising: a) providing a protein mixture comprising non-PEGylated protein, mono-PEGylated protein and oligo-PEGylated protein; b) subjecting the protein mixture to a two-stage hydrophobic interaction chromatography (HIC) step, comprising: applying the protein mixture to a first HIC material to provide a first HIC flow-through solution; and applying the first HIC flow-through solution to a second HIC material to provide a second HIC flow-through solution, wherein the second HIC material is different from the first HIC material; and wherein the two-stage HIC step is performed under two-stage HIC conditions, which two-stage HIC conditions are suitable for binding oligo-PEGylated protein to the first HIC material and binding mono-PEGylated protein to the second HIC material; and c) eluting the mono-PEGylated protein from the second HIC material to provide a second HIC eluate, wherein the second HIC eluate provides the mono-PEGylated protein composition.

The protein may be EPO. The protein may be a hormone. The protein may be a hormone, a cytokine, an enzyme or an antibody.

The two-stage HIC conditions may alternatively be referred to as a single set of conditions, or fixed conditions. There is no adjustment of the HIC conditions between application of the protein mixture to the first HIC material and application of the first HIC flow-through solution to the second HIC material. The two-stage HIC conditions are the salt, pH buffer and pH conditions used in the two-stage HIC step. The two-stage HIC conditions may refer to the composition of the protein mixture (or load composition), equilibration buffer, and wash buffer used in the two-stage HIC step.

The term "conditions" in context of the present disclosure refers to the composition of the mobile phase. In particular it refers to the type and concentration of salt in the mobile phase. It may also refer to the type and concentration of other substituents in the mobile phase such as pH buffer or detergent.

The protein mixture is applied across both HIC materials in the two-stage HIC step. The first HIC flow-through solution may be applied directly to the second HIC material with no intervening conditioning or adjustment step. The first HIC material and second HIC material may be directly connected. The first HIC material and second HIC material may be directly connected in series. For example the first HIC material is comprised in a first HIC column and the second HIC material is comprised in a second HIC column, and the first HIC column is directly connected to the second HIC column. The first HIC flow-through solution from the first HIC column may be directly delivered to the second HIC column. There may be an in-line connection between the first HIC column and the second HIC column. There may be a mechanism that permits continuous flow between the first HIC column and the second HIC column. The steps of the process may be performed continuously. The steps of the process may be performed in parallel, that is, step (b) may be begun before step (a) is completed, such that steps (a) and (b) run in parallel. Performing the process continuously (or in parallel) is advantageous because it is relatively fast and efficient.

The steps of the process of the invention may be performed sequentially. The process may comprise the sequential steps of: (a) providing a protein mixture comprising non-PEGylated protein, mono-PEGylated protein and oligo-PEGylated protein; (b) subjecting the protein mixture to a two-stage hydrophobic interaction chromatography (HIC) step, comprising: applying the protein mixture to a first HIC material to provide a first HIC flow-through solution; and applying the first HIC flow-through solution to a second HIC material to provide a second HIC flow-through solution, wherein the second HIC material is different from the first HIC material; and wherein the two-stage HIC step is performed under two-stage HIC conditions, which two-stage HIC conditions are suitable for binding oligo-PEGylated protein to the first HIC material and binding mono-PEGylated protein to the second HIC material; and (c) eluting the mono-PEGylated protein from the second HIC material to provide a second HIC eluate, wherein the second HIC eluate provides the mono-PEGylated protein composition.

The term "sequential" means that no intervening chromatography step and/or no intervening conditioning or adjustment step occurs between any of steps a to c (no interventing step between steps (a) and (b), or (b) and (c)). The term "sequential" means that no intervening step occurs between any of the steps recited in any one of the claims. The steps of the processes of the invention may be performed directly, meaning that each of steps (b) and (c) is performed directly following the previous step. The process may consist of steps (a) to (c). The process may consist of the steps recited in any one of the claims. The process may be performed continuously and sequentially.

The first HIC material and second HIC material are different from each other. They may be different in terms of the type of ligand, and/or the degree of substitution of the ligand (the density of the ligand). The first HIC material may be more hydrophilic than the second HIC material. The first HIC material may be Phenyl Sepharose HP. The second HIC material may be Toyopearl Phenyl 650M.

Under the two-stage HIC conditions, the first HIC material does not bind, or does not significantly bind, non-PEGylated protein. Under the two-stage HIC conditions, the second HIC material does not bind, or does not significantly bind non-PEGylated protein. The fraction of non-PEGylated protein in the first HIC flow-through solution and/or in the second HIC flow-through solution is substantially the same as in the protein mixture.

Under the two-stage HIC conditions, the first HIC material does not bind, or does not significantly bind mono-PEGylated protein. The fraction of mono-PEGylated protein in the first HIC flow-through solution is substantially the same as in the protein mixture.

In the present context the term "does not significantly bind" may mean that the HIC material binds less than about 5%, 2%, 1%, 0.5%, 0.1% or 0.01% of the protein species referred to. In the present context the term a fraction of a protein species that is "substantially the same" is within about ±0.1%, 0.5%, 1%, 2.5%, 5%, or 10% of the reference value. For example a first HIC flow-through solution that contains a fraction of mono-PEGylated protein that is substantially the same as that in the protein mixture may contains a proportion of mono-PEGylated protein that is within about ±1% of the proportion of mono-PEGylated protein in the protein mixture.

In the processes disclosed herein the first HIC material is more hydrophilic than the second HIC material, expressed alternatively, the second HIC material is more hydrophobic than the second HIC material. The first HIC material may be determined as more hydrophilic than the second HIC material because in a comparative chromatogram it elutes mono-PEGylated protein first. The retention time for mono-PEGylated protein during gradient elution is less for the first HIC material than for the second HIC material.

Reference to dynamic binding capacity herein refers to the dynamic binding capacity under the conditions chosen for the chromatography process or step. The dynamic binding capacity of a chromatography medium under particular chromatography conditions for a particular protein can be thought of as the maximum amount of that protein that can be loaded onto the chromatography medium without causing unnecessary protein loss. That is, the maximum amount of protein of interest that can be loaded without causing "breakthrough". Protein breakthrough may be monitored by spectrophotometry for example at 280 nm ($A_{280}$). The breakthrough threshold may be 10%. The chromatography conditions may be the pH, conductivity and flow rate, and the concentrations of any salts or other additives to the mobile phase. The dynamic binding capacity of the first or second HIC material may be determined under the operating conditions for the two-stage HIC processes of the invention. For example the two-stage HIC conditions may be conditions under which the first HIC material has a relatively high dynamic binding capacity for oligo-PEGylated protein. The two-stage HIC conditions may be conditions under which the second HIC material has a relatively high binding capacity for mono-PEGylated protein. The two-stage HIC conditions and HIC materials may be selected to adjust, or optimise, the dynamic binding capacity of the first HIC and second HIC materials in order that oligo-PEGylated protein is retained (bound tightly) by the first HIC material and mono-PEGylated protein is retained (bound tightly) by the second HIC material.

The two-stage HIC conditions may be such that the amount of oligo-PEGylated protein applied to the first HIC material is lower than, or about 80-95% of, or about 2, 5, 10, 20 or 30 times lower than the dynamic binding capacity of the first HIC material for oligo-PEGylated protein. The two-stage HIC conditions may be such that substantially no oligo-PEGylated protein "breaks through" the first HIC material. The two-stage HIC conditions may be such that most, or substantially all, of the oligo-PEGylated protein is retained by the first HIC material. The first HIC material, under the two-stage HIC conditions, may have a dynamic binding capacity for oligo-PEGylated protein that is higher than, or about 2, 5, 10, 20 or 30 times higher than, the amount of oligo-PEGylated protein loaded onto the material. Using a first HIC material with a relatively low dynamic binding capacity for oligo-PEGylated protein is advantageous for example because a relatively large amount of protein (a relatively large amount of protein mixture) can be loaded onto the first HIC material. This enables for example use of a smaller column, which is economically advantageous.

The two-stage HIC conditions may be such that the amount of mono-PEGylated protein applied to the second HIC material is lower than, or about 80-95% of, or about 2, 5, 10, 20 or 30 times lower than the dynamic binding capacity of the second HIC material for mono-PEGylated protein. The second HIC material, under the two-stage HIC conditions, may have a dynamic binding capacity for mono-PEGylated protein that is higher than, or about 2, 5, 10, 20 or 30 times higher than, the amount of mono-PEGylated protein loaded onto the material. Using a second HIC material with a relatively low dynamic binding capacity for mono-PEGylated protein is advantageous for example because a relatively large amount of protein (a relatively large amount of the first HIC flow-through solution) can be loaded onto the second HIC material. This enables for example use of a smaller column, which is economically advantageous.

In comparative HIC elution chromatograms the first HIC material and the second HIC material may have well-resolved elution peaks for mono-PEGylated protein. Well-resolved peaks are peaks with little or no overlap. In comparative HIC elution chromatograms the first HIC material and the second HIC material may have elution peaks for mono-PEGylated protein for which $R_s$ is at least, or at least about, 0.8, 1.0, 1.2 or 1.5.

The first HIC material may be Phenyl Sepharose HP (for example HiTrap Phenyl HP; GE Healthcare). The first HIC material may be an HIC material having substantially the same selectivity as Phenyl Sepharose HP. The first HIC material may be an HIC material having substantially the same selectivity as Phenyl Sepharose HP for mono-PEGylated EPO in a falling gradient from 500 mM to 0 mM $Na_2SO_4$, in 25 mM HEPES, pH 7.5 at room temperature. The protein may be erythropoietin.

The second HIC material may be Toyopearl Phenyl 650M (Tosoh Bioscience LLC). The second HIC material may be an HIC material having substantially the same selectivity as Toyopearl Phenyl 650M. The second HIC material may be an HIC material having substantially the same selectivity as Toyopearl Phenyl 650M for mono-PEGylated EPO in a falling gradient from 500 mM to 0 mM $Na_2SO_4$, in 25 mM HEPES, pH 7.5 at room temperature. The protein may be erythropoietin.

Substantially the same selectivity for mono-PEGylated EPO may refer to having the substantially the same elution peak maxima, which may mean a retention time or volume ±10%, or may refer to having a resolution in a comparative chromatogram for which $R_s$ is at least, or at least about, 0.8, 1.0, 1.2 or 1.5.

A HIC material used in the processes disclosed herein may comprise a phenyl ligand. It may comprise a methacrylic resin functionalised with a phenyl ligand. The HIC material may comprise a basal matrix of Sepharose or hydroxylated methacrylic polymer. HiTrap Phenyl HP (high performance) comprises a basal matrix of Sepharose with a phenyl ligand at a ligand density of 25 µmol/mL medium. The first HIC material may comprise a basal matrix (for example a Sepharose matrix) with a phenyl ligand at about 20-30 µmol/mL medium, or about 25 µmol/mL medium. The second HIC material may comprise a basal matrix (for example a Sepharose matrix) with a phenyl ligand at about 40-50 µmol/mL medium, or about 40 or 50 µmol/mL medium. Toyopearl Phenyl 650M comprises a basal matrix of hydroxylated methacrylic polymer with a phenyl ligand. The second HIC material may comprise a basal matrix of hydroxylated methacrylic polymer with a phenyl ligand. The first HIC material may be more hydrophilic than the second HIC material. The HIC materials used in the processes disclosed herein may be used in accordance with the manufacturer's instructions.

In the processes disclosed herein mono-PEGylated protein is eluted from the second HIC material to provide a second HIC eluate (step c). The second HIC eluate provides a mono-PEGylated protein composition. The second HIC eluate comprises an increased fraction of mono-PEGylated protein relative to the protein mixture. The second HIC eluate may comprise at least 90%, 95%, 98%, 99%, 99.5%, or 99.9% mono-PEGylated protein. The mono-PEGylated protein may be eluted from the second HIC material by a linear gradient, which may be a falling salt concentration. The mono-PEGylated protein may be eluted from the second HIC material by a step gradient, which may be a decreased salt concentration.

The processes disclosed herein may comprise eluting oligo-PEGylated protein from the first HIC material to provide a first HIC eluate. The "first HIC eluate" may also be referred to as the "first HIC material eluate", because it is the eluate from the first HIC material in the two-stage HIC step. The first HIC eluate provides an oligo-PEGylated protein composition. The first HIC eluate comprises an increased fraction of oligo-PEGylated protein relative to the protein mixture. The first HIC eluate may comprise at least 90%, 95%, 98%, 99%, 99.5%, or 99.9% oligo-PEGylated protein. The oligo-PEGylated protein may be eluted from the linear HIC material by a linear gradient, which may be a falling salt concentration. The oligo-PEGylated protein may be eluted from the first HIC material by a step gradient, which may be a decreased salt concentration.

The protein mixture comprises non-PEGylated, mono-PEGylated and oligo-PEGylated protein. It may have substantially the same composition of additives as the equilibration buffer used in the two-stage HIC step. It may have substantially the same composition of additives as the high salt buffer (buffer A). Such a protein mixture may also be referred to herein as a load composition, load solution, or sample. The protein mixture may be prepared by concentrating the protein, for example by centrifugation, and suspending in a high salt buffer. The protein mixture may be prepared by buffer exchange. The protein mixture or load composition may have a protein concentration of 0.1-1.0 mg/mL, 0.2-0.5 mg/mL, or about 0.25 mg/mL. Protein concentration can be determined by UV spectroscopy at 280 nm.

The HIC processes disclosed herein involve buffers of various salt concentrations. The processes may involve using a high salt buffer (buffer A) and a low salt buffer (buffer B) and preparing various other buffer solutions using varying proportions of buffer A and buffer B.

The high salt buffer (buffer A) comprises salt, which may be may be $Na_2SO_4$. The salt may be $(NH_4)_2SO_4$, $Na_2SO_4$, NaCl, KCl and $CH_3COONH_4$. The high salt buffer may comprise 400-600 mM $Na_2SO_4$, 450-550 mM $Na_2SO_4$, or about 500 mM $Na_2SO_4$. The high salt buffer may comprise an alternative salt at the same concentrations as mentioned for 400-600 mM $Na_2SO_4$, or at concentrations that provide equivalent ionic strength or conductivity. The high salt buffer may comprise a pH buffer, such as HEPES. For example it may comprise about 10-50 mM pH buffer, about 20-30 mM pH buffer or about 25 mM pH buffer, which may be HEPES. The high salt buffer may have a pH of about 7.0-8.0, or about 7.5. The high salt buffer may comprise about 25 mM HEPES, at about pH 7.5, and about 500 mM $Na_2SO_4$. The high salt buffer may have a conductivity of about 40-80 mS/cm, 50-70 mS/cm, 55-65 mS/cm or about 60 mS/cm.

The low salt buffer (buffer B) comprises no salt or a low concentration of salt. The low salt buffer may comprise less than 10 mM salt. The low salt buffer may have the same pH buffer, at substantially the same concentration, and substantially the same pH as the high salt buffer. The low salt buffer may have a conductivity of about 0.5-5 mS/cm, 0.5-2.5 mS/cm, or about 1 mS/cm. The low salt buffer may have a conductivity of less than about 5 mS/cm or 2.5 mS/com.

The protein mixture may have substantially the same salt, pH buffer, and pH as the high salt buffer. For example the protein mixture (or load composition, or sample) may comprise non-PEGylated protein, mono-PEGylated protein and oligo-PEGylated protein in a solution of 25 mM HEPES, pH 7.5, 500 mM $Na_2SO_4$.

The HIC materials may be equilibrated before the protein mixture is applied to them for the two-stage HIC step. The equilibration buffer has a relatively high salt concentration. The equilibration buffer may comprise about 10-20% buffer B and remainder buffer A. The equilibration buffer may comprise 13.5% buffer B and 86.5% buffer A. The equilibration buffer may comprise a pH buffer, such as HEPES. For example it may comprise about 10-50 mM pH buffer, about 20-30 mM pH buffer or about 25 mM pH buffer, which may be HEPES. The equilibration buffer may have a pH of about 7.0-8.0, or about 7.5. The equilibration buffer may have a salt concentration of about 400-450 mM, or about 420-450 mM or about 432.5 mM salt, which may be $Na_2SO_4$. The equilibration buffer may have a conductivity of about 50-60 mS/cm, or about 54-55 mS/cm, or about 54.5 mS/cm.

After the protein mixture has been applied to the first HIC material the first and second HIC materials may be washed with a wash buffer as part of the two-stage HIC step. The wash buffer for the two-stage HIC step may be the same as the equilibration buffer. The wash buffer comprise about 10-50 mM pH buffer, about 20-30 mM pH buffer or about 25 mM pH buffer, which may be HEPES. The wash buffer may have a pH of about 7.0-8.0, or about 7.5. The wash buffer may have a salt concentration of about 400-450 mM, or about 420-450 mM or about 432.5 mM salt, which may be $Na_2SO_4$. The wash buffer may have a conductivity of about 50-60 mS/cm, or about 54-55 mS/cm, or about 54.5 mS/cm. At least 3, 5, or 10 column volumes (CVs) of wash buffer may be used, or 2-25, 5-20, 10-20 or about 15 CVs of wash buffer may be used.

After the HIC materials have been washed in the two-stage HIC step, mono-PEGylated protein is eluted from the second HIC material to provide a second HIC eluate (step c). The elution of the second HIC material may comprise a step elution. The step elution may use an elution buffer that is about 30-50% buffer B and remainder buffer A, or about 40% buffer B and remainder buffer A. The elution buffer may comprise a pH buffer, such as HEPES. For example it may comprise about 10-50 mM pH buffer, about 20-30 mM pH buffer or about 25 mM pH buffer, which may be HEPES. The elution buffer may have a pH of about 7.0-8.0, or about 7.5. The elution buffer may have a salt concentration of about 250-350 mM, 275-325 mM or about 300 mM salt, which may be $Na_2SO_4$. The elution buffer may have a conductivity of about 35-45 mS/cm, 40-45 mS/cm, or about 41.25 mS/cm. The step elution may comprise the use of about 5-10, or about 8 CVs of elution buffer. The elution buffer may have a conductivity at least 2, 3, 4, 5, 6, 7, 8, 9, 10, or 15 mS/cm lower than the conductivity of the two-stage HIC conditions.

The elution of the second HIC material may further comprise a gradient elution to about 70-90%, 75-85% or about 80% buffer B, over about 5-20, or 10-15 CVs or within 10 CVs, or within 14 or 15 CVs. The gradient elution may be to about 50-200 mM, 50-150 mM, 75-125 mM or about 100 mM salt, which may be $Na_2SO_4$.

Oligo-PEGylated protein may be eluted from the first HIC material (step d). The elution of the first HIC material may comprise washing with wash buffer for 5-10 or about 8 CVs, then applying an elution gradient to at least 90% or to 100% buffer B within 10, 15 or 20 CVs and eluting with this buffer for a further 5-10 or 8 CVs.

The HIC materials may be regenerated with pure water.

The processes disclosed herein are particularly suitable for preparing a mono-PEGylated protein composition from a protein mixture that comprises a relatively high proportion of oligo-PEGylated protein. The processes disclosed herein may be used with protein mixtures that comprise at least 50%, 5%, 10%, 15%, 20%, 25%, or 30% oligo-PEGylated protein, or about 5-20% or 10-30% oligo-PEGylated protein.

Figure 5:
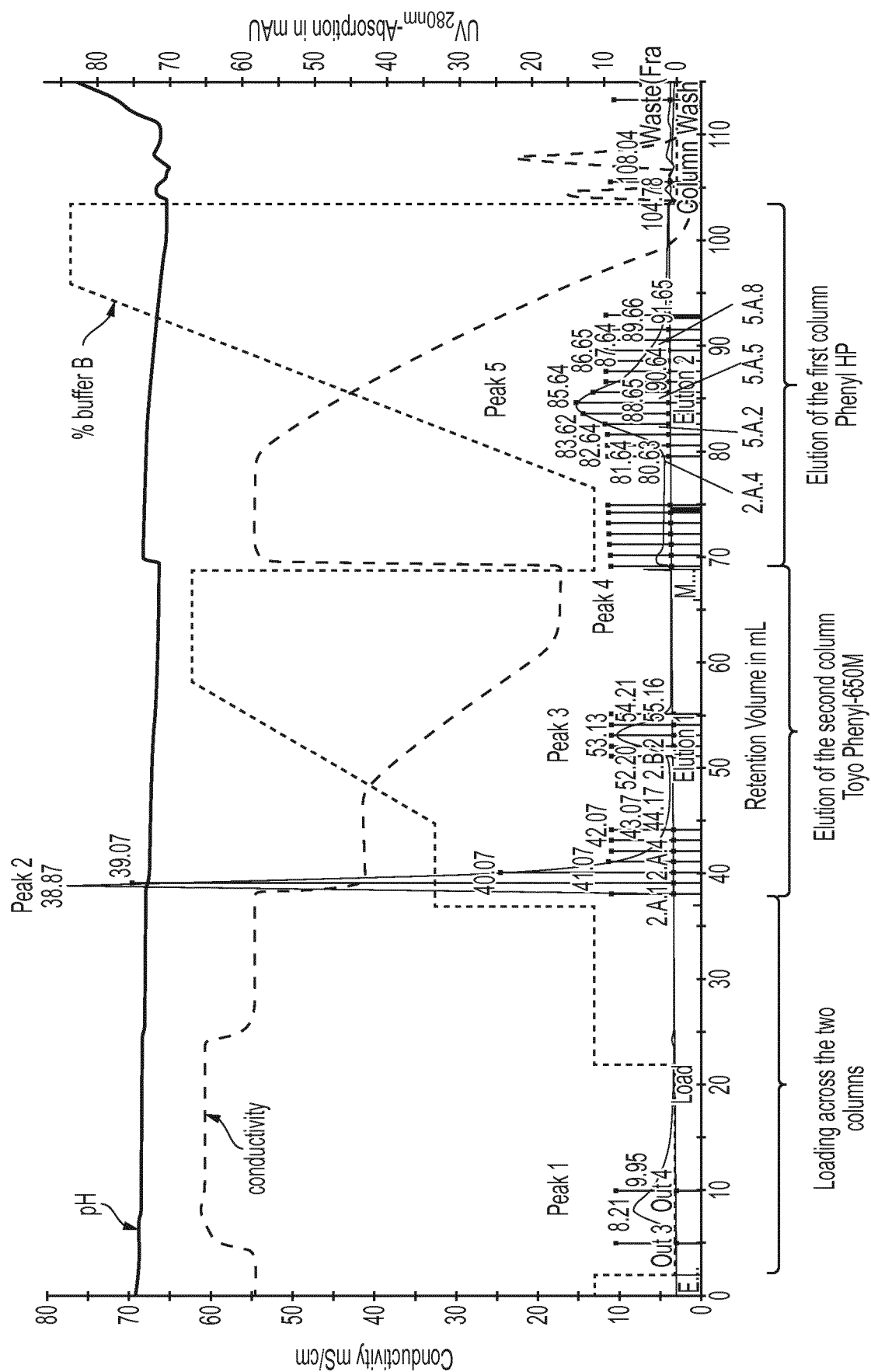
FIG. 5. Chromatogram of the column combination (column of first HIC material and column of second HIC material). During loading via both columns non-PEGylated EPO is in the flow-through solutions. Elution of the second column at 41 mS/cm shows that mainly mono-PEGylated EPO elutes in the step elution, but some oligo-PEGylated EPO elutes in the gradient elution. During elution of the second column, starting at 54.5 mS/cm, small amounts of mono-PEGylated EPO elute. In the gradient, oligo-PEGylated EPO elutes completely. The pH value is approximately 7.5 throughout. The proportion of low salt buffer B, increasing from 0% to 100%, is shown, as is the conductivity of the fractions. The compositions of peaks 1 to 5 are summarised in Table 6 below.

The processes disclosed herein may provide a mono-PEGylated protein composition of relatively high purity. As described below, a mono-PEGylated protein composition (a second HIC eluate) containing 100% mono-PEGylated EPO was prepared using the processes described herein (Table 4). Peak 2 of FIG. 5 is a second HIC eluate and comprises 100% mono-PEGylated EPO.

The processes disclosed herein may provide a relatively high yield, such that a relatively high proportion of the mono-PEGylated protein in the starting sample (the protein mixture) is recovered in the mono-PEGylated protein composition. The processes disclosed herein may provide a mono-PEGylated protein composition in which at least about 70%, 75%, 80%, or 85% of the mono-PEGylated protein is recovered from the protein mixture. As described below, about 89.5% of the mono-PEGylated EPO was recovered from a PEGylation reaction sample (protein mixture) using the processes disclosed herein (Table 7).

The processes disclosed herein may provide a relatively high yield, such that a relatively high proportion of the non-PEGylated protein in the starting sample (the protein mixture) is recovered in the second HIC flow-through solution, this non-PEGylated protein can be recycled. The processes disclosed herein may provide a second HIC flow-through solution in which at least about 80%, 85%, 90%, 95%, 98%, 99%, or 99.9% of the non-PEGylated protein from the protein mixture is recovered. As described below, about 100% of the non-PEGylated EPO was recovered from a PEGylation reaction sample (protein mixture) using the processes disclosed herein (Table 7).

The processes disclosed herein may provide a mono-PEGylated protein composition of relatively high purity.

The pH of the HIC conditions should be suitable for protein stability and activity. The pH may be about 5.0-8.5. Physiological pH may be desirable, particularly for therapeutic or biologically active proteins.

Selection of pH buffers is usually not critical for HIC. Phosphate buffers, or HEPES buffers, or other Good's buffers may be used. Buffers having a pKa from about 6-10 may be used. Buffers that do not contain a primary amine are particularly suitable (because a primary amine may act as a partner for the PEG reagent resulting in some PEGylated buffer molecules).

Flow rates for chromatography steps may be selected and adjusted according to conventional techniques. Faster flow rates will decrease binding capacity, which means that a balance may be reached between achieving maximum dynamic binding capacity and a fast separation, particularly when applying large volumes of protein mixtures to be separated. Suitable flow rates may be 50-400 cm/h. Residence times may be 3-5 minutes, or possibly less, depending on the chromatography material used. Faster flow rates and shorter residence times may be desirable for improving overall process productivity.

Chromatography steps may be performed under conditions "suitable for binding" a particular protein (or PEGylation form of a protein). The skilled person is familiar with chromatography techniques and is able to find conditions suitable for binding a particular protein empirically, using his common general knowledge and guided by the present disclosure. Parameters such as chromatography material, type and/or concentration of salt, pH, buffers, temperature and flow rate can all be altered to provide conditions suitable for binding a particular protein (or PEGylation form of a protein) in chromatography.

In the present context, chromatography steps may remove a "contaminant" from a mixture or a solution (such as a protein mixture or a first HIC flow-through solution), wherein the contaminant is an undesired form of protein. A contaminant may also be referred to as an impurity. For example, since the desired form of protein in the present context is mono-PEGylated protein, the chromatography step may remove non-PEGylated protein or oligo-PEGylated protein. The chromatography step may also remove other contaminants, such as protein aggregates, or PEGylation reactants.

PEG

Poly(ethylene glycol) or PEG is a neutral hydrophilic polyether. The term "molecular weight" (in kDa) in the present context is to be understood as the mean molecular weight of the PEG because PEG as polymeric compound is not obtained with a defined molecular weight but in fact has a molecular weight distribution; the term "about" indicates that some PEG molecules, or residues, will weigh more and some less than the indicated molecular weight, i.e. the term "about" in this context may refer to a molecular weight distribution in which 95% of the PEG molecules have a molecular weight within +/−10% of the indicated molecular weight. For example, a molecular weight of 30 kDa may denote a range of from 27 kDa to 33 kDa.

A PEG residue can contain further chemical groups which are necessary for binding reactions, which results from the chemical synthesis of the PEGylated molecule, or which is a spacer for optimal distance of parts of the molecule. These further chemical groups are not used for the calculation of the molecular weight of the PEG residue. In addition, such a PEG residue can consist of one or more PEG chains which are covalently linked together. PEG residues with more than one PEG chain are called multiarmed or branched PEG residues. Branched PEG residues can be prepared, for example, by the addition of polyethylene oxide to various polyols, including glycerol, pentaerythriol, and sorbitol. Branched PEG residues are reported in, for example, EP 0 473 084, U.S. Pat. No. 5,932,462. A PEG molecule used in a PEGylation reaction, and a PEG residue on a PEGylated protein, may each have a molecular weight of at least about 12 kDa, or at least about 20 kDa, about 20 kDa to 40 kDa, or about 30 kDa. A PEG residue may have a molecular weight of 20 kDa to 35 kDa and be a linear PEG residue. A PEG residue may have a molecular weight of 35 kDa to 40 kDa and be a branched PEG residue.

A mono-PEGylated EPO may comprise a single PEG residue having a molecular weight of at least about 12 kDa, or at least about 20 kDa, about 20 kDa to 40 kDa, about 20 kDa, or about 30 kDa. A PEG residue may have a molecular weight of at least about 20 kDa.

A mono-PEGylated protein is a protein comprising a single PEG residue. That is, the mono-PEGylated protein has one PEG residue only. An oligo-PEGylated protein comprises at least two PEG residues. For example an oligo-PEGylated protein may be a di-, tri or tetra-PEGylated protein. The term oligo-PEGylated protein (or poly-PEGylated protein) may refer to a group of oligo-PEGylated protein molecules having varying degrees of PEGylation (two, three, or more PEG residues). The term PEGylated protein refers to mono-PEGylated and oligo-PEGylated proteins. The term PEGylated protein may refer to protein consisting of mono-PEGylated and oligo-PEGylated protein. A non-PEGylated protein is a protein that does not comprise any PEG residues. A non-PEGylated protein may also be referred to in the context of a PEGylation reaction as an unreacted protein. A non-PEGylated protein may be referred to as a native protein, or an un-PEGylated protein or a free protein.

The term "PEGylation" means a covalent linkage of a PEG residue with a protein. In particular it may refer to a covalent linkage at the N-terminus of the polypeptide and/or an internal lysine residue. PEGylation of proteins is widely known in the state of the art and reviewed by, for example, Veronese, F. M., Biomaterials 22 (2001) 405-417. PEG can be linked using different functional groups and polyethylene glycols with different molecular weight, linear and branched PEGs as well as different linking groups (see also Francis, G. E., et al., Int. J. Hematol. 68 (1998) 1-18; Delgado, C., et al., Crit. Rev. Ther. Drug Carrier 30 Systems 9 (1992) 249-304). PEGylation of erythropoietin can be performed in aqueous solution with PEGylation reagents as described, for example, in WO 00/44785, in one embodiment by using NHS-activated linear or branched PEG molecules of a molecular weight between 5 kDa and 40 kDa. PEGylation can also be performed at the solid phase according to Lu, Y., et al., Reactive Polymers 22 (1994) 221-229. Not randomly, N-terminally PEGylated polypeptide can also be produced according to WO 94/01451. PEGylation reactions are also reviewed in WO 2009/010270 and WO 2012/035037.

Suitable PEG derivatives are activated PEG molecules with an average molecular weight of from about 5 to about 40 kDa, or from about 20 to about 40 kDa. The PEG derivative is in one embodiment a linear or a branched PEG. A wide variety of PEG derivatives suitable for use in the preparation of PEG-protein and PEG-peptide conjugates can be obtained from Shearwater Polymers (Huntsville, Ala., U.S.A.; www.nektar.com). Activated PEG derivatives are known in the art and are described in, for example, Morpurgo, M., et al., J. Bioconjug. Chem. 7 (1996) 363-368.

A PEGylation reaction may be performed at a pH of about 6.5 to 9.5, about 7.0 to 9.0, or about 7.5 to 8.5, or about 8.0. The pH at which the PEGylation reaction is performed may depend on the PEG reagent used. The PEG reagent may be mPEG-NHS, mPEG-SPA, mPEG-SVA or mPEG-Cl. The PEGylation reaction may be performed at a pH of about 7.0 to 9.0, or about 7.5 to 8.5, or about 8.0 using (NHS) activated PEG reagent. The PEGylation reaction may be performed at about 15-25° C., or about 18-22° C., or about 20° C. The PEGylation reaction may be carried out for at least about 20, 30, 40, 50 or 60 minutes, or about 30-90, or 30-60 minutes, or about 40, 50, or 60 minutes.

A PEGylation reaction may be performed in a solution comprising a salt and a buffer. The salt may be $Na_2SO_4$ and the buffer may be bicine. The salt may be present in an amount of 5-10 mM or about 7.5 mM. The buffer may be present in an amount of about 10-50 mM, 20-30 mM or about 25 mM. The PEGylation reaction may be performed in 7.5 mM $Na_2SO_4$ and 25 mM bicine.

The pH of the PEGylation reaction may be the substantially same as the pH of the two-stage HIC conditions. The pH of the PEGylation reaction may be selected to be substantially the same as the pH of two-stage HIC conditions, such that the protein mixture resulting from the PEGylation reaction is loaded directly onto the first HIC material. In this context substantially the same means within 1.0, 0.9, 0.8, 0.6, 0.7, 0.5, 0.4, 0.3, 0.2, or 0.1 pH units. In such processes the protein mixture is the mixture of reaction products that results from the PEGylation reaction. Such processes are relatively efficient and fast. In this context "loaded directly" means that no pH adjustment of the mixture of reaction products is carried out before it is applied to the first HIC material. The buffer for the PEGylation reaction may be the same as the buffer for two-stage HIC conditions.

EPO

The term "erythropoietin" and its abbreviation "EPO" refer to a protein having the amino acid sequence of SEQ ID NO: 1 or of SEQ ID NO: 2, or a protein or polypeptide substantially homologous thereto, whose biological properties relate to the stimulation of red blood cell production and the stimulation of the division and differentiation of committed erythroid progenitors in the bone marrow. Recombinant erythropoietin may be prepared via expression in eukaryotic cells, for example in CHO cells, or BHK cells, or HeLa cells by recombinant DNA technology or by endogenous gene activation, i.e. the erythropoietin glycoprotein is expressed by endogenous gene activation, see for example U.S. Pat. Nos. 5,733,761, 5,641,670, 5,733,746, WO 93/09222, WO 94/12650, WO 95/31560, WO 90/11354, WO 91/06667, and WO 91/09955. The EPO may be human EPO. The EPO may be glycosylated EPO.

The human EPO may have the amino acid sequence set out in SEQ ID NO: 1 or SEQ ID NO: 2. The human EPO may have the amino acid sequence set out in SEQ ID NO: 1. The term "EPO" also denotes variants of the protein of SEQ ID NO: 1 or of SEQ ID NO: 2, in which one or more amino acid residues have been changed, deleted, or inserted, and which has comparable biological activity as the not modified protein, such as e.g. reported in EP 1 064 951 or U.S. Pat. No. 6,583,272. The number of amino acids changed, deleted or inserted may be 1, 2, 3, 4, 5, 6, 7, 8, 9, 10, 1-50, 1-40, 1-30, 1-20, or 1-10. The term EPO denotes proteins that comprise or consist of the amino acid sequence set out in SEQ ID NO:1 or SEQ ID NO:2 or variants thereof. A variant may have the amino acid sequence of human erythropoietin having from 1 to 6 additional sites for glycosylation. The specific activity of PEGylated erythropoietin can be determined by various assays known in the art. The biological activity of the purified PEGylated erythropoietin are such that administration of the protein by injection to human patients results in bone marrow cells increasing production of reticulocytes and red blood cells compared to noninjected or control groups of subjects. The biological activity of PEGylated erythropoietin obtained and purified in accordance with the method as reported herein can be tested by methods according to Bristow, A, *Pharmeuropa Spec. Issue Biologicals BRP Erythropoietin Bio* 97-2 (1997) 31-48.

Amino acid sequence variants of EPO can be prepared by introducing appropriate modifications into the nucleotide sequence encoding the EPO, or by peptide synthesis. Such modifications include, for example, deletions from, and/or insertions into, and/or substitutions of residues within the amino acid sequences of the erythropoietin. Any combination of deletion, insertion, and substitution can be made to arrive at the final construct, provided that the final construct possesses comparable biological activity to the human EPO.

Conservative amino acid substitutions are shown in Table 1 under the heading of "preferred substitutions". More substantial changes are provided in Table 1 under the heading of "exemplary substitutions", and as described below in reference to amino acid side chain classes. Amino acid substitutions may be introduced into human erythropoietin and the products screened for retention of the biological activity of human erythropoietin.

Non-conservative substitutions will entail exchanging a member of one of these classes for another class.

The EPO may be a variant EPO. The EPO may be comprised in a fusion protein with another protein, or may be conjugated to another moiety in addition to PEG.

The chemical PEGylation of erythropoietin generally results in a protein preparation comprising erythropoietin which is PEGylated at one or more ε-amino groups of lysine residues and/or at the N-terminal amino group. Selective PEGylation at the N-terminal amino acid can be performed according to Felix (1997). Selective N-terminal PEGylation can be achieved during solid-phase synthesis by coupling of a $N^\alpha$-PEGylated amino acid derivative to the N−1 terminal amino acid of the peptide chain. Side chain PEGylation can be performed during solid-phase synthesis by coupling of $N^\epsilon$-PEGylated lysine derivatives to the growing chain. Combined N-terminal and side chain PEGylation is feasible either as described above within solid-phase synthesis or by solution phase synthesis by applying activated PEG reagents to an amino deprotected peptide.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Val; Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Proteins

The processes of the invention are especially suitable for producing mono-PEGylated EPO compositions. Reference to a protein or protein of interest herein may refer to EPO.

The processes of the invention may be suitable for producing mono-PEGylated protein compositions of other proteins, particularly therapeutic proteins. For example interleukin-2 (IL-2), peginterferon alfa-2a, human growth hormone (hGH), bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, granulocyte colony stimulating factor (G-CSF), granulocyte-macrophage colony stimulating factor (GM-CSF), interferon alpha, interferon beta, interferon gamma, tissue-type plasminogen activator (IPA), leptin, hirudin, urokinase, human DNase, insulin, hepatitis B surface protein (HbsAg), chimeric diphtheria toxin-IL-2, human chorionic gonadotropin (hCG), thyroid peroxidase (TPO), alpha-galactosidase, alpha-L-iduronidase, beta-glucosidase, alpha-galactosidase A, acid a-glucosidase (acid maltase), anti-thrombin III (AT III), follicle stimulating hormone (FSH), glucagon-like peptide-I (GLP-1), glucagonlike peptide-2 (GLP-2), fibroblast growth factor 7 (FGF-7), fibroblast growthfactor 21 (FGF-21), fibroblast growth factor 23 (FGF-23), Factor X, Factor XIII, prokinetisin, extend in-4, CD4, tumor necrosis factor receptor (TNF-R), a-$CD_{20}$, P-selectin glycoprotein ligand-I (PSGL-I), complement, transferrin, glycosylation-dependent cell adhesion molecule (GlyCAM), neural-cell adhesion molecule (N-CAM), INF receptor-IgG Fe region fusion protein. Such proteins also include antibodies such as monoclonal antibodies against any one of: respiratory syncytial virus, protein F of respiratory syncytial virus, INF-a, glycoprotein IIb/IIIa, CD20, VEGF-A, PSGL-1, CD4, a-CD3, EGF, carcinoembryonic antigen (CEA), TNFα and IL-2 receptor.

The processes of the invention may be suitable for producing mono-PEGylated compositions of proteins such as hormones, cytokines or enzymes. Such a protein may be erythropoietin. The protein may be interferon-α-2a or interferon-α-2b. The protein may be granulocyte colony-stimulating factor, human growth hormone, or urate oxidase.

The invention is particularly useful for therapeutic proteins having a relatively short half-life, because PEGylation increases in vivo circulation half-life. Generally hormones and cytokines have a relatively short half-life. Smaller biological molecules tend to have a relatively short half-life. The pharmacokinetic profile of relatively small biological molecules may be improved by PEGylation and so the present invention may also be particularly useful for relatively small therapeutic proteins. Generally proteins and peptides smaller than approximately 70 kDa are more likely to be eliminated by kidney filtration than are larger proteins. Smaller biological molecules, or proteins, may be defined as those having a molecular weight of less than about 70 kDa. Erythropoietin has a molecular weight of about 37 kDa. The invention is useful for therapeutic proteins having a molecular weight less than about 70 kDa (in their non-PEGylated form). The invention is useful for therapeutic proteins having a molecular weight less than about 70 kDa, 60 kDa, 50 kDa, or 40 kDa, or having a molecular weight of about 10-70 kDa, 20-60 kDa, 20-50 kDa, or 30-40 kDa. The invention is useful for hormones or cytokines having a molecular weight less than about 70 kDa, 60 kDa, 50 kDa, or 40 kDa, or having a molecular weight of about 10-70 kDa, 20-60 kDa, 20-50 kDa, or 30-40 kDa.

The protein may be an antibody. An antibody may be a polyclonal antibody or a monoclonal antibody. An antibody may be a biologically functional antibody fragment. Antibody fragments include Fab, Fab', F(ab')$_2$, scFv, (scFv)$_2$, single-domain antibodies (sdAb, or dAB), complementarity determining region fragments, linear antibodies, single-chain antibody molecules, minibodies, diabodies and multispecific antibodies formed from antibody fragments. Many antibody fragments have a relatively short half-life in vivo, which results from their relatively small size and their no longer having an Fc region. The invention is particularly useful for antibody fragments having a relatively small size, such as single-domain antibodies, Fabs, Fab's, and scFvs. The invention is useful for antibody fragments having a molecular weight less than about 70 kDa, 60 kDa, 50 kDa, or 40 kDa, or having a molecular weight of about 10-70 kDa, 20-60 kDa, 20-50 kDa, or 30-40 kDa.

The mono-PEGylated protein compositions may be formulated as pharmaceutical compositions. The mono-PEGylated protein compositions produced by the processes disclosed herein may be formulated with one or more pharmaceutically acceptable excipients, and/or may be formulated in a physiologically acceptable buffer such as physiological saline. The salts and/or buffers used in the equilibration, wash, or elution buffers of the HIC step may be removed before formulating the mono-PEGylated protein composition as a pharmaceutical composition. For example the mono-PEGylated protein compositions may be dialysed. The mono-PEGylated protein of the mono-PEGylated protein composition may be lyophilised. The mono-PEGylated protein of the mono-PEGylated protein composition may be isolated and reformulated in a pharmaceutical composition.

The processes of the disclosed herein may be industrial scale processes. An industrial scale process may be a process that produces at least about 5 g, 10 g, 25 g, 50 g, 100 g, 250 g or 500 g per batch or per cycle. A batch or cycle in this context may be a process comprising all of the steps a) to c) as disclosed herein. An industrial scale process may be a process in which the volume of the protein mixture (comprising non-PEGylated, mono-PEGylated and oligo-PEGylated protein) that is subjected to the HIC steps is at least 100 L, 500 L, 1000 L, 5000 L, 10000 L, 50000 L, or 100000 L.

Room temperature may be about 18-25° C., 20-22° C., about 20° C., about 21° C. or about 22° C. The processes disclosed herein may be performed at room temperature. HIC may be performed at room temperature. HIC may be performed at a temperature of 15-25° C. For reproducibility processes may perform HIC at a specific and stable temperature. A stable temperature may be a specific temperature ±1.0° C. or ±1.0° C. The process may be performed at any temperature from about 4 to 40° C., provided that the protein is stable under such conditions.

The invention includes the combination of the aspects and preferred features described except where such a combination is clearly impermissible or expressly avoided.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

All references mentioned above are hereby incorporated by reference.

EXAMPLES

Example 1

Preparation of PEGylated EPO for Chromatography
Materials:
0.87 mg/mL of recycled PEGylated erythropoietin in 10 mM Na/K phosphate 100 mM NaCl, pH 7.5 (PEG molecule used in PEGylation reactions and PEG residues on a PEGylated protein each having molecular weight of about 30 kDa)
High salt buffer (25 mM HEPES, 500 mM $Na_2SO_4$, pH 7.5 sterile filtered)
Centrifugal concentrators 10 kDa MWCO Vivaspin 20 (Sartorius #VS2002)
Chromatography For high-salt chromatography the PEGylated erythropoietin may undergo buffer exchange and be concentrated. For this purpose, 7 mL of PEGylated erythropoietin are pipetted into a 10 kDa MWCO centrifugal concentrator and centrifuged for 40 min at 4,700 g. Subsequently, the mixture is subjected to buffer exchange with 10 mL of high-salt buffer and centrifuged again for 40 minutes at 4,700 g. If, in one of the steps, the concentrate volume is >0.5 mL, the centrifugation is extended accordingly. After the buffer exchange, about 0.2 mL of retentate is dissolved in 3 mL of high-salt buffer and the concentration is determined spectrophotometrically at 280 nm.

Before each chromatography, the EPO concentrate thus prepared is diluted with high salt buffer to a concentration of 0.25 mg/mL for the loading of the column. As a rule, the column is loaded with 2 mL, which corresponds to a 0.5 mg sample. The loading concentration is determined by means of UV/Vis spectroscopy at 280 nm.

After the PEGylation of erythropoietin, non-PEGylated erythropoietin (EPO) and singly PEGylated erythropoietin (mono-PEG EPO) should be separated from multiply PEGylated erythropoietin (oligo-PEG EPO).

After the evaluation of the various chromatography media, the purification should be tested by two-step chromatography. For this purpose, two columns are selected for the experiment and are connected in series in the ÄKTA in such a way that, with the same salt concentration, more hydrophobic analytes (oligo-PEG-EPO) bind to the first column, whilst more hydrophilic analytes (mono-PEG-EPO) bind to the second column. Very hydrophilic analytes (unPEGylated EPO) should not bind but elute during the sample application. In addition, it is necessary to control the columns independently of each other in order to elute the analytes of the column separately from each other.

The mobile phase A consists of 25 mM HEPES 500 mM $Na_2SO_4$, pH 7.5 (about 60 mS/cm). The mobile phase B consists of 25 mM HEPES, pH 7.5 (about 1 mS/cm). The volume flow is adjusted to 61.5 cm/h and the chromatography is carried out at room temperature. The conductivities determined in FIG. 1 cannot be directly incorporated into the chromatography program. Rather, the conductivity may be adjusted by varying the proportions of the mobile phases (%-B). The resulting fractions of the mobile phases are then incorporated into the chromatography program.

The equilibration of the column is initially carried out with 13.5% buffer B. The column is then loaded with 2 mL of the prepared sample via the sample pump. Thereafter, the columns are washed with 13.5% buffer B for 15 CV and the starting conditions for the elution are adjusted. Since EPO is in the run, the run is fractionated from the 3rd CV to the 13th CV for further analyses.

The elution of the second column is started first because the desired product mono-PEG-EPO should be eluted earlier to facilitate faster process times. The elution of the mono-PEG-EPO begins with a step elution to 40% B (41.25 mS/cm) for 8 CV followed by a gradient to 80% B within 14 CV. The 80% B are held for a further 8 CV and the elution is thus terminated.

The second elution, which elutes the oligo-PEG-EPO of the first column, begins with 13.5% B for 8 CV followed by a gradient to 100% B within 20 CV. The 100% B are then held for a further 8 CV and the elution is thus terminated.

The column washing and the cleaning in place (CIP) step are performed simultaneously for both columns at an increased flow of 1 ml/min (186.5 cm/h). For this, the second column is connected again and both columns are washed in ultra-pure water for 8 CV. The run is collected completely in one fraction.

Example 2

High Performance Liquid Chromatography (HPLC)

The composition of the collected fractions of the HIC is analysed using HPLC.

Equipment

Dionex UltiMate 3000 HPLC System (Thermo Fisher Scientific Inc.)

RP-$C_{18}$ column, RP-Poroshell 300SB 2.1×75 mm; 300 Å (Agilent Technologies)

The collected frozen HIC fractions are thawed, in each case 100 μL sample pipetted into the auto-sampler vials and placed in the auto sampler which has been cooled to 10° C. 25 μL of sample are applied, heated for 0.5 min in the column oven at 60° C. and applied to the column. The flow rate is 1 mL/min. After the test run, the chromatography begins with a gradient from 40% B to 52% B within 4 minutes. Thereafter, the 52% B is held for 3 minutes. During this time, pure EPO (non-PEG) usually elutes in the gradient. The second gradient is then made from 52% to 58% B within 3 min followed by 4 min hold at 58% B. During the gradient from 52% to 58% or shortly thereafter, mono-PEG-EPO usually elutes. Elution of the oligo-PEG-EPO takes place in the one-minute gradient from 58% B to 62% B. The 62% B are held for a further 4 minutes. Then the regeneration of the column with 100% B takes place for 1 min.

The proportions of the components in the sample are determined by integration of the UV chromatogram. For this purpose, the integration limits are set at the corresponding peaks with the aid of software. The areas are then calculated. The proportion p of the respective component is calculated as follows:

$$p\_Component\ in\ \% = \frac{area\ of\ the\ peak\ of\ the\ component}{area\ of\ all\ peaks} * 100\%$$

Example 3

HIC Material Screening

Figure 2:
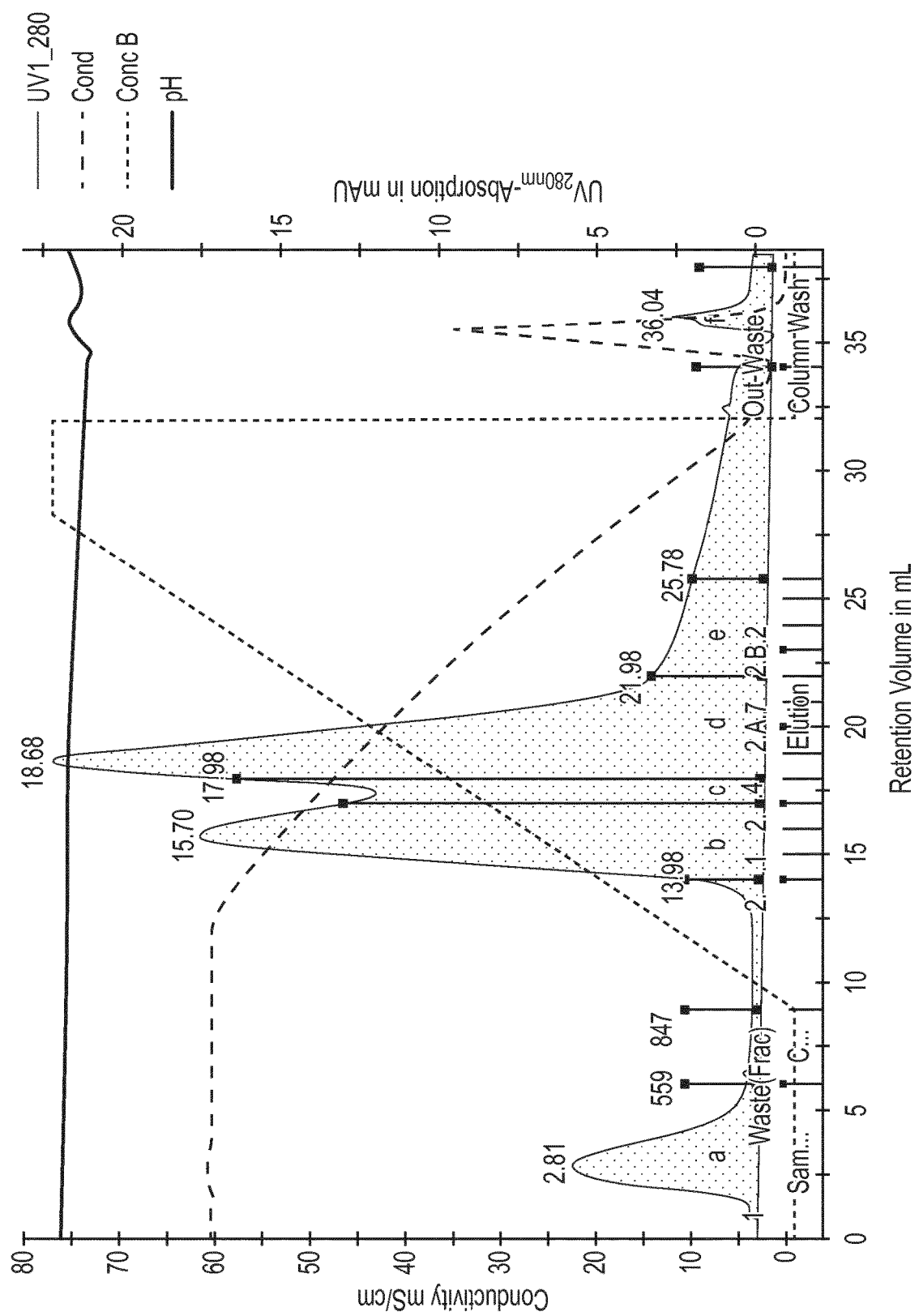
FIG. 2. Detailed chromatogram of Phenyl Sepharose HP. The vertical lines indicate the fractions a-f collected for HPLC analysis. The pH value is approximately 7.5 throughout. The proportion of low salt buffer B, increasing from 0% to 100%, is shown, as is the conductivity of the fractions.
Figure 3:
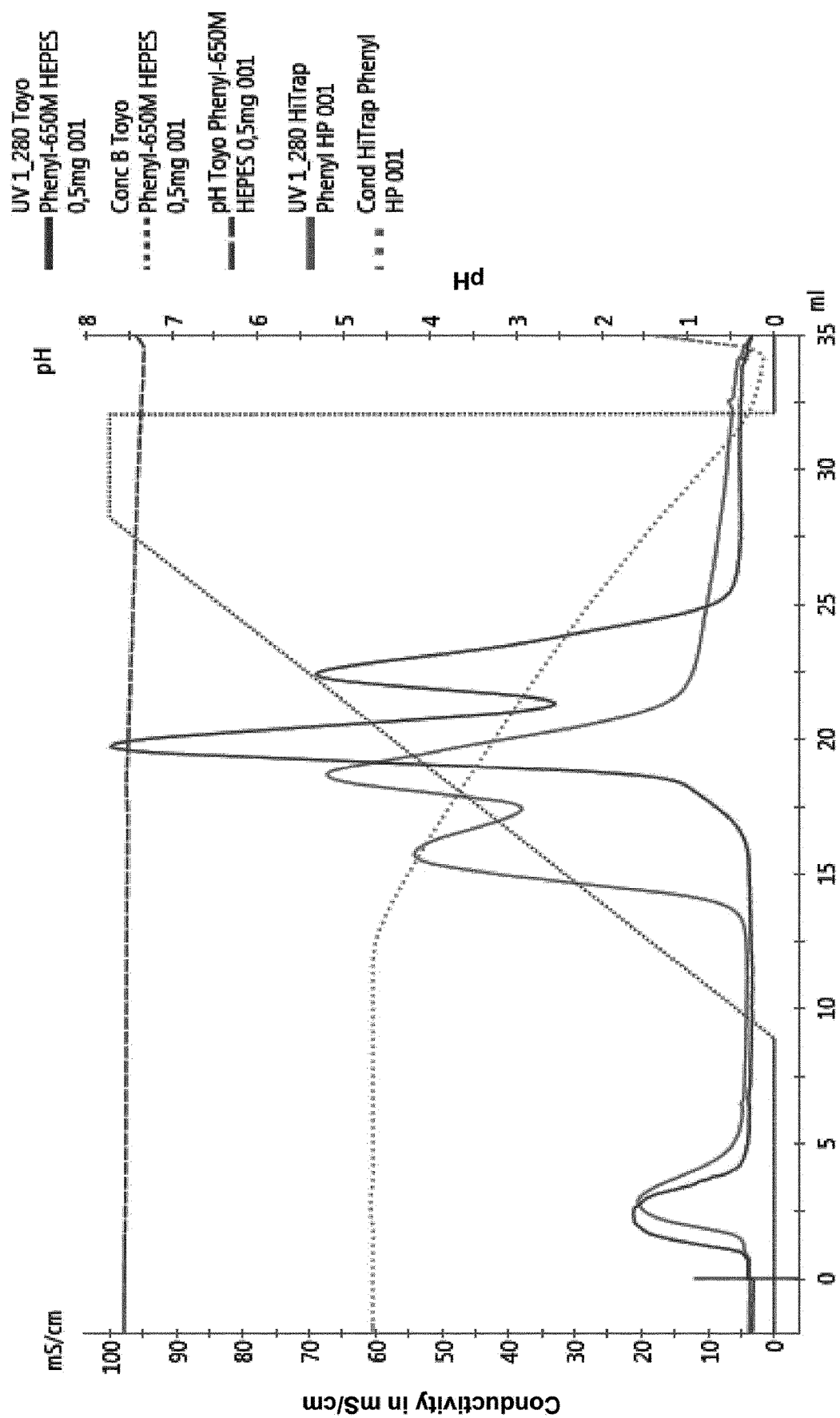
FIG. 3. Comparative chromatogram. Comparison of the UV chromatograms of Phenyl Sepharose HP and Toyopearl Phenyl 650M columns. The trace with the earliest mono-PEGylated EPO peak is Phenyl Sepharose HP, and the remaining trace is Toyopearl Phenyl 650M. The pH value is approximately 7.5 throughout. The proportion of low salt buffer B, increasing from 0% to 100%, is shown, as is the conductivity of the fractions from the Phenyl Sepharose HP column.

Sixteen HIC materials were screened for selectivity (e.g. well separated elution peaks) for non-PEGylated, mono-PEGylated and oligo-PEGylated protein. Three HIC materials (Toyopearl PPG-600M and Toyopearl Phenyl-650M from Tosoh Bioscience LLC, and Phenyl Sepharose HP (HiTrap Phenyl HP) from GE Healthcare) showed the best selectivity compared to the remaining columns and can be described as columns with medium hydrophobicity. The chromatograms are similar to each other in profile. They consist of three peaks each. The first peak appears during loading of the column, the second and third peaks appear as a wide double peak during the gradient. During the washing step with water, the fourth peak appears. The HiTrap Phenyl HP in FIG. 2 is an example of these three columns. However, it differs in the retention volume of the peaks and in the peak shape from the other two columns. After reaching the maximum, the third peak initially decreases roughly as strongly as in the other two columns, but progresses towards the end and does not reach the baseline until the washing step. On the other hand, the other two columns again reach the base line after the third peak has fallen.

For better comparison, the UV chromatograms of the three columns are shown in FIG. 1. In addition, the conductivity is plotted for the phenyl HP as an example, so that later the composition of the mobile phase for the elution of the individual components can be estimated. This figure shows, above all, in addition to the similar elution profiles, the differences between the columns with respect to the elution volumes. In Table 1, in addition, the retention volumes of the peaks are listed at the maximum. The device error for the retention volume depends primarily on the flow rate of the pump and is specified by the manufacturer at 1.5%, and the error due to different gel charges and column packs is estimated to be 5%, which means the total error is 6.5%. The first peak (maximum) is very close to 2.2 mL for the Toyopearl PPG and 2.8 mL for the Phenyl Sepharose HP, but for all three columns, the retention volumes of the second and third peaks differ more markedly. The retention volume for peak 2 is 19.8 mL and peak 3 is 22.4 mL. Thus the retention volumes for the Toyopearl Phenyl 650M are greater than those of PPG-600M and Phenyl Sepharose HP. The Phenyl Sepharose HP has the lowest retention volumes with 15.7 mL for peak 2 and 18.7 mL for peak 3. Retention volumes of the Toyopearl PPG-600M are closer to those of the Phenyl Sepharose HP than the Toyopearl Phenyl-650M.

The peaks of the analytes eluting in the Toyopearl Phenyl-650M and Phenyl Sepharose HP during the gradient show the greatest differences in retention volume (4.1 mL at peak 2 and 3.7 mL at peak 3). On the other hand, the difference between the retention volumes between the Toyopearl PPG-600M and the Phenyl Sepharose HP is rather small and the peaks overlap extensively.

The conductivity of the mobile phases for the column combination is determined by means of the conductivity and the elution profile in FIG. 1. During loading the conductivity of the mobile phase should be 54.5 mS/cm. With this conductivity, EPO is in the run and can be reused immediately. Oligo-PEG-EPO should bind to the first column (green, Phenyl Sepharose HP). Mono-PEG-EPO and potentially breaking-through oligo-PEG-EPO, on the other hand, bind only on the second column (orange, Toyopearl Phenyl-650M). Elution of the product mono-PEG-EPO takes place by elution of the second column at 41 mS/cm (orange).

TABLE 1

Comparison of the retention volumes (in mL) of the three main peaks of the three most selective columns. 6.5% is assumed as a total error.

| Columns | Toyopearl Phenyl-650M | Toyopearl PPG-600M | Phenyl Sepharose HP |
|---|---|---|---|
| Peak 1 | 2.3 ± 0.2 | 2.2 ± 0.1 | 2.8 ± 0.2 |
| Peak 2 | 19.8 ± 1.3 | 16.9 ± 1.1 | 15.7 ± 1.0 |
| Peak 3 | 22.4 ± 1.5 | 19 ± 1.2 | 18.7 ± 1.2 |

The desired salt concentrations for the elution of the components can be estimated over the course of the conductivities of the chromatographic sequences.

Mass Balance

The mass balances for the chosen columns are shown in Table 2. The amount of sample injected into the sample loop is listed as input. As described above, the concentration of the sample was determined undiluted using a photometer. This was then injected into the sample loop. It follows that the error for the input depends mainly on the device error and is 1%. The output represents the amount of sample calculated during the entire chromatography run, starting at the injection through the end of the elution, via the measurement of absorption and integration of the absorption curve. The error is mainly related to the measurement of the flow rate and the UV measurement. The flow rate error is 1.5% if the pump runs properly. The UV measurement error is indicated by the manufacturer at 2.0%. The random error is estimated to be 10% since only single measurements are available. The total error is therefore 13.5%. Table 2: Comparison of the amount of sample in mg before the application to the column with the amount of eluted sample shows good agreement with respect to the measurement accuracy. The amount of the input was determined by a photometer, while the amount of the output was determined by integrating the UV chromatograms.

TABLE 2

| Mass balance | Input/mg | Output/mg |
|---|---|---|
| Phenyl Sepharose HP | 0.50 ± 0.01 | 0.53 ± 0.07 |
| Toyopearl PPG-600M | 1.02 ± 0.01 | 1.07 ± 0.14 |
| Toyopearl Phenyl-650M | 0.48 ± 0.01 | 0.50 ± 0.07 |

Example 4

Characterisation of the Separation by HPLC

In order to check the separation of the sample components EPO, mono-PEG-EPO and oligo-PEG-EPO during chromatography, six fractions were collected for each chromatographic run and characterised by HPLC. The letters a f are assigned to the characterized fractions, which are indicated for Phenyl Sepharose HP in FIG. 2 in order to be able to compare the results in Table 3 more easily with the chromatograms of the HIC.

TABLE 3

The composition of the peaks in the chromatogram was characterized by HPLC analysis. The respective proportions p in % of EPO (non-PEG), mono-PEG-EPO (mono) and oligo-PEG-EPO (oligo) are listed for each collected fraction. The positions of the fractions (a-f) are shown in the respective chromatogram. LOD: limit of detection <0.2%.

| Column | Position of the fraction | Fraction | $p_{non-PEG}$/% | $p_{mono}$/% | $p_{oligo}$/% |
|---|---|---|---|---|---|
| Phenyl Sepharose HP | Peak 1 | a | 100.0 | LOD | <LOD |
| | Peak 2 | b | 0.7 | 99.3 | <LOD |
| | Transition | c | 0.3 | 77.0 | 22.7 |
| | Peak 3 | d | 0.3 | 35.0 | 64.7 |
| | | e | <LOD | 43.7 | 56.3 |
| | Washing step | f | <LOD | <LOD | <LOD |
| Toyopearl Phenyl-650M | Peak 1 | a | 100.0 | <LOD | <LOD |
| | Peak 2 | b | <LOD | 100.0 | <LOD |
| | | c | <LOD | 96.9 | 3.1 |
| | Transition | d | <LOD | 69.7 | 30.3 |
| | Peak 3 | e | <LOD | 16.4 | 83.6 |
| | Washing step | f | LOD | <LOD | <LOD |
| Toyopearl PPG-600M | Peak 1 | a | 100.0 | <LOD | <LOD |
| | Peak 2 | b | <LOD | 99.4 | 0.6 |
| | | c | <LOD | 93.0 | 7.0 |
| | Transition | d | <LOD | 47.7 | 52.3 |
| | Peak 3 | e | <LOD | 12.5 | 87.5 |
| | Washing step | f | <LOD | <LOD | <LOD |

From the results of the HPLC analysis, it is seen that the run in all three columns during the loading of the sample is 100% non-PEGylated EPO. Peak 2 consists largely of mono-PEG-EPO and peak 3 of oligo-PEG-EPO. However, the composition of peak 2 and peak 3 differs in the different columns. The Phenyl Sepharose HP also contains 0.7% EPO in peak 2 in addition to 99.3% mono-PEG-EPO. In Peak 2 of the Toyopearl Phenyl-650M and PPG-600M, however, EPO can no longer be detected. Peak 2, Peak 3 and the transition consists of different proportions of mono-PEG-EPO and oligo-PEG-EPO. In Toyopearl Phenyl, the proportion of mono-PEG-EPO in the peak 2 fraction b is 100% and in the Toyopearl PPG-600M, it is 99.4% mono-PEG-EPO.

Example 5

Implementation of the Column Combination

Toyopearl Phenyl-650M and Phenyl Sepharose HP were well suited as chromatography media for the separation of EPO, mono-PEG-EPO and oligo-PEG-EPO under the two-stage HIC conditions used herein. Phenyl Sepharose HP (less hydrophobic than Toyopearl Phenyl-650M) is used as the first column. Toyopearl Phenyl-650M (more hydrophobic) is used as the second column. FIG. 5 shows the chromatogram of the combination of these two columns. A total of 5 peaks are recognizable. The first peak is the run during the sample application over the two columns. The second and third peaks appear respectively during the elution of the Toyopearl Phenyl-650M. Peaks four and five appear during the elution of the Phenyl Sepharose HP. The pH falls from pH 7.6 to 7.3 during the chromatography, rises to a pH value of 7.5 at the beginning of the second elution and drops to pH 7.2 by the washing step. The column was equilibrated with 13.5% B, which corresponds to a conductivity of 54.6 mS/cm. During the sample application, the conductivity rises to 60.7 mS/cm and then falls again to 54.6 mS/cm. The first Elution begins with a step at 40% B, which corresponds to a conductivity of 41.3 mS/cm. In the stage of 40% B, the largest peak appears, which makes up 49% of the total area under the UV chromatogram. In the gradient to 80% B, the third peak appears; this is significantly smaller, with 7.5 area percent. The second elution (Phenyl Sepharose HP) starts at equilibration conditions with 13.5% B. Elution begins with the smallest peak in the chromatogram, which accounts for 3.4 area percent. In the subsequent gradient to 100% B the second largest peak then appears with 28.0 area percent.

Next, the composition of the collected fractions was determined by HPLC analysis. In Table 4 the compositions of the individual peaks of EPO (non-PEG), mono-PEG-EPO (mono) and oligo-PEG-EPO (oligo) are listed. Peak 1 thus consists of 100% EPO. Peak 2 consists of 100% mono-PEG-EPO. The other peaks, on the other hand, are mixtures of mono-PEG-EPO and oligo-PEG-EPO. The output represents the composition of the total eluted material. For this, the amounts of protein determined by absorption were divided by their composition in the peaks. Thus, the extent to which the composition of the input (load) changes during chromatography can be compared. Since the reaction is self-contained, the composition of the input should match that of the output.

TABLE 4

The composition of the peaks was determined by HPLC analysis. The composition of the output was calculated. LOD: limit of detection <0.2%.

|  | $p_{non-PEG}/\%$ | $p_{mono}/\%$ | $p_{oligo}/\%$ |
| --- | --- | --- | --- |
| Input (Load) | 9.2 | 52.8 | 38.0 |
| Output | 10.6 | 55.1 | 34.3 |
| Peak 1 | 100.0 | <LOD | <LOD |
| Peak 2 | <LOD | 100.0 | <LOD |
| Peak 3 | <LOD | 1.5 | 98.5 |
| Peak 4 | <LOD | 57.0 | 43.0 |
| Peak 5 | <LOD | 13.3 | 86.7 |
| Washing step | <LOD | 11.9 | 88.1 |

The comparison of the composition of the input with that of the output is represented in Table 5 by calculation of the recovery. The recovery is calculated as follows:

$$\text{Recovery \%} = \frac{p_{Output}}{p_{Input}} * 100\%$$

The recovery is calculated separately for each share p of the components.

TABLE 5

Calculation of the recovery in % The composition of the input is compared with the composition of the total eluted sample material (output). The respective method of analysis with which the composition was determined is indicated in brackets.

|  | $p_{non-PEG}/\%$ | $p_{mono}/\%$ | $p_{oligo}/\%$ |
| --- | --- | --- | --- |
| Input (HPLC) | 9.22 | 52.76 | 38.02 |
| Output (OD$_{280}$ and HPLC) | 10.59 | 55.13 | 34.28 |
| Recovery/% | 114.9 | 104.5 | 90.2 |

Likewise the mass balance should be equalised, like the recovery. The masses of the individual components obtained are shown in Table 6. It is noteworthy that the applied mass of (1.54±0.21) mg protein deviates strongly from the calculated mass of (1.03±0.14) mg in the output. As a result of the usual visual inspection, leakage of the system and resulting sample loss can be ruled out. Because of this marked deviation of 33%, further calculations of yields and losses will refer to the calculated mass in the output of the 1.03 mg sample.

TABLE 6

The amounts of protein collected in the peaks were calculated via the composition of the peaks (HPLC analysis) and the integration of the UV absorptions in the chromatogram. LOD = limit of detection.

|  | Fraction | $m_{non-PEG}$/mg | $m_{mono}$/mg | $m_{oligo}$/mg | $m_{total}$/mg | Application |
| --- | --- | --- | --- | --- | --- | --- |
| Output | Total | 0.11 ± 0.01 | 0.57 ± 0.08 | 0.35 ± 0.05 | 1.03 ± 0.14 | Load |
|  | Peak 1 | 0.11 ± 0.01 | <LOD | <LOD | 0.11 ± 0.01 | Re-PEGylation |
|  | Peak 2 | <LOD | 0.51 ± 0.07 | <LOD | 0.51 ± 0.07 | Product |
|  | Peak 3 | <LOD | <LOD | 0.08 ± 0.01 | 0.08 ± 0.01 | Waste |
|  | Peak 4 | <LOD | 0.02 ± 0.01 | 0.01 ± 0.01 | 0.03 ± 0.02 | Waste |
|  | Peak 5 | <LOD | 0.04 ± 0.01 | 0.24 ± 0.03 | 0.28 ± 0.04 | Waste |
|  | Washing step | <LOD | <LOD | 0.02 ± 0.01 | 0.02 ± 0.01 | Waste |

Table 7 shows the yields and losses resulting in the two-step chromatography. If we consider peak 1, which represents the EPO peak, 100% of the loaded EPO can be recovered for reuse. The yield in respect of the total amount of mono-PEG-EPO in the load is 89.5% when peak 2 is collected. The loss of 40.0% total protein refers to the total protein mass in the load, which would occur during the chromatography by discarding peaks 3, 4 and 5. As listed in Table 6 these peaks contain mainly oligo-PEG EPO and only small amounts of mono-PEG-EPO.

TABLE 7

Yields and losses of the useful fractions (see Table 6) in the two-step chromatography performed. The yields refer to the total proportion of the respective component in the output. The loss refers to the total sample (1.03 mg).

| EPO yield for re-PEGylation | 100.0% |
| --- | --- |
| mono-PEG-EPO yield as product | 89.5% |
| Total waste fractions (oligo- and mixed fractions) | 40.0% |

REFERENCES

A number of publications are cited above in order to more fully describe and disclose the invention and the state of the art to which the invention pertains. Full citations for these references are provided below. The entirety of each of these references is incorporated herein.

For standard molecular biology techniques, see Sambrook, J., Russel, D. W. *Molecular Cloning, A Laboratory*

Manual. 3 ed. 2001, Cold Spring Harbor, New York: Cold Spring Harbor Laboratory Press.
Bristow, A, Pharmeuropa Spec. Issue Biologicals BRP Erythropoietin Bio 97-2 (1997) 31-48
Delgado, C., et al., Crit. Rev. Ther. Drug Carrier 30 Systems 9 (1992) 249-304)
Fee & Van Alstine, Chemical Engineering Science, 2016, 61, 924-939
Felix, A. M., ACS Symposium Series, 680: 218-238, (1997)
Francis, G. E., et al., Int. J. Hematol. 68 (1998) 1-18
Hydrophobic Interaction and Reversed Phase Chromatography, Principles and Methods, GE Handbook, 2006
Ingold et al, React. Chem. Eng., 2016, 1,218.
Lu, Y., et al., Reactive Polymers 22 (1994) 221-229
Morpurgo, M., et al., J. Bioconjug. Chem. 7 (1996) 363-368.
Pfister et al, Reac React. Chem. Eng., 2016, 1,204
Pfister et al. Biotechnology and Bioengineering, 2016, 113, 1711-1718.
Veronese, F. M., Biomaterials 22 (2001) 405-417.
WO 94/12650
WO 90/11354
WO 91/06667
WO 91/09955
WO 93/09222
WO 94/01451
WO 95/31560
WO 00/44785
WO 2009/010270
WO 2012/035037
EP 0 473 084
EP 1 064 951
U.S. Pat. No. 5,733,761
U.S. Pat. No. 5,641,670
U.S. Pat. No. 5,733,746
U.S. Pat. No. 5,932,462
U.S. Pat. No. 6,583,272

The following numbered statements relate to aspects of the present disclosure and form part of the description.

1. A process for producing a mono-PEGylated protein composition comprising at least about 90% mono-PEGylated protein, the process comprising:
    a) providing a protein mixture comprising non-PEGylated protein, mono-PEGylated protein and oligo-PEGylated protein;
    b) subjecting the protein mixture to a two-stage hydrophobic interaction chromatography (HIC) step, comprising:
        applying the protein mixture to a first HIC material to provide a first HIC flow-through solution; and
        applying the first HIC flow-through solution to a second HIC material to provide a second HIC flow-through solution,
        wherein the second HIC material is different from the first HIC material; and
        wherein the two-stage HIC step is performed under two-stage HIC conditions, which two-stage HIC conditions are suitable for binding oligo-PEGylated protein to the first HIC material and binding mono-PEGylated protein to the second HIC material; and
    c) eluting the mono-PEGylated protein from the second HIC material to provide a second HIC eluate, wherein the second HIC eluate provides the mono-PEGylated protein composition.
2. The process according to statement 1, wherein the protein is a hormone or a cytokine.
3. The process according to statement 2, wherein the protein is erythropoietin.
4. A process for producing a mono-PEGylated protein composition comprising at least about 90% mono-PEGylated protein, wherein the protein is erythropoietin, the process comprising:
    a) providing a protein mixture comprising non-PEGylated protein, mono-PEGylated protein and oligo-PEGylated protein;
    b) subjecting the protein mixture to a two-stage hydrophobic interaction chromatography (HIC) step, comprising:
        applying the protein mixture to a first HIC material to provide a first HIC flow-through solution; and
        applying the first HIC flow-through solution to a second HIC material to provide a second HIC flow-through solution,
        wherein the second HIC material is different from the first HIC material; and
        wherein the two-stage HIC step is performed under two-stage HIC conditions, which two-stage HIC conditions are suitable for binding oligo-PEGylated protein to the first HIC material and binding mono-PEGylated protein to the second HIC material; and
    c) eluting the mono-PEGylated protein from the second HIC material to provide a second HIC eluate, wherein the second HIC eluate provides the mono-PEGylated protein composition.
5. The process according to anyone of the preceding statements wherein the first HIC material and the second HIC material are directly connected in series.
6. The process according to any one of the preceding statements, wherein under the two-stage HIC conditions the first HIC material does not bind non-PEGylated protein or mono-PEGylated protein, and wherein the second HIC material does not bind non-PEGylated protein.
7. The process according to any one of the preceding statements, wherein in comparative HIC elution chromatograms the first HIC material and the second HIC material have well-resolved peaks for mono-PEGylated protein.
8. The process according to any one of the preceding statements, wherein
    a) the first HIC material has substantially the same selectivity as Phenyl Sepharose HP under the two-stage HIC conditions; and
    b) the second HIC material has substantially the same selectivity as Toyopearl Phenyl 650M under the two-stage HIC conditions.
9. The process according to any one of the statements, wherein
    a) the first HIC material is Phenyl Sepharose HP; and/or
    b) the second HIC material is Toyopearl Phenyl 650M.
10. The process according to statement 8 or statement 9, wherein the protein is erythropoietin.
11. The process according to any one of the preceding statements, comprising the further step of:
    d) eluting the oligo-PEGylated protein from the first HIC material to provide a first HIC eluate.
12. The process according to statement 11, wherein eluting the oligo-PEGylated protein from the first HIC material comprises a linear gradient elution.

13. The process according to any one of the preceding claims, wherein
   i. the two-stage HIC conditions are at a conductivity of about 54-55 mS/cm; and/or
   ii. eluting the mono-PEGylated protein from the second HIC material is at a conductivity of about 40-41 mS/cm; and/or
   iii. eluting the oligo-PEGylated protein from the first HIC material is carried out by linear gradient from about 54-55 mS/cm to about 1-5 mS·cm.
14. The process according to any one of the preceding claims, wherein the process is carried out using a mixture of buffer A and buffer B, wherein buffer A comprises 25 mM HEPES, pH 7.5, 500 mM Na₂SO₄, and wherein buffer B comprises 25 mM HEPES, pH 7.5, and wherein
   i. the two stage HIC conditions are at about 13.5% buffer B; and/or
   ii. eluting the mono-PEGylated protein from the second HIC material is at about 40% buffer B; and/or
   iii. eluting the oligo-PEGylated protein from the first HIC material is carried out by linear gradient from about 13.5% to about 80% buffer B.
15. The process according to statement 13 or 14, wherein the protein is erythropoietin.
16. The process according to statement 10 or 15, wherein the mono-PEGylated erythropoietin comprises a PEG residue having a molecular weight of at least about 20 kDa.
17. The process according to any one of the preceding statements, wherein elution of the mono-PEGylated protein from the second HIC material comprises a step elution followed by a gradient elution.
18. The process according to any one of the preceding statements, wherein the mono-PEGylated protein composition comprises at least about 99% mono-PEGylated protein.
19. The process according to any one of the preceding statements, wherein the protein mixture comprises at least 10% oligo-PEGylated protein.
20. The process according to any one of the preceding statements, wherein the mono-PEGylated protein comprises a PEG residue having a molecular weight of at least about 20 kDa.
21. The process according to any one of the preceding statements wherein the mono-PEGylated protein composition is a pharmaceutical composition, the process further comprising formulating the second HIC eluate with a pharmaceutical excipient.

The invention claimed is:

1. A process for producing a mono-PEGylated protein composition comprising at least about 90% mono-PEGylated protein, comprising the steps of:
   a) providing a protein mixture comprising non-PEGylated protein, mono-PEGylated protein and oligo-PEGylated protein;
   b) subjecting the protein mixture to a two-stage hydrophobic interaction chromatography (HIC) step, comprising:
      applying the protein mixture to a first HIC material to provide a first HIC flow-through solution; and
      applying the first HIC flow-through solution to a second HIC material to provide a second HIC flow-through solution,
      wherein the second HIC material is different from the first HIC material; and
      wherein the two-stage HIC step is performed under two-stage HIC conditions, which two-stage HIC conditions are suitable for binding oligo-PEGylated protein to the first HIC material and binding mono-PEGylated protein to the second HIC material; and
   c) eluting the mono-PEGylated protein from the second HIC material to provide a second HIC eluate, wherein the second HIC eluate provides the mono-PEGylated protein composition.

2. The process according to claim 1, wherein the protein is a hormone, a cytokine, an enzyme or an antibody.

3. The process according to claim 1, wherein the protein is erythropoietin.

4. The process according to claim 1, wherein the first HIC material and the second HIC material are directly connected in series.

5. The process according to claim 1, wherein under the two-stage HIC conditions the first HIC material does not bind non-PEGylated protein or mono-PEGylated protein, and wherein the second HIC material does not bind non-PEGylated protein.

6. The process according to claim 1, wherein in comparative HIC elution chromatograms the first HIC material and the second HIC material have well-resolved peaks for mono-PEGylated protein.

7. The process according to claim 1, wherein
   a) the first HIC material has substantially the same selectivity as Phenyl Sepharose HP under the two-stage HIC conditions; and
   b) the second HIC material has substantially the same selectivity as Toyopearl Phenyl 650M under the two-stage HIC conditions.

8. The process according to claim 1, wherein
   a) the first HIC material is Phenyl Sepharose HP; and/or
   b) the second HIC material is Toyopearl Phenyl 650M.

9. The process according to claim 1, comprising the further step of:
   d) eluting the oligo-PEGylated protein from the first HIC material to provide a first HIC eluate.

10. The process according to claim 9, wherein eluting the oligo-PEGylated protein from the first HIC material comprises a linear gradient elution.

11. The process according to claim 1, wherein
   i. the two-stage HIC conditions are at a conductivity of about 54-55 mS/cm; and/or
   ii. eluting the mono-PEGylated protein from the second HIC material is at a conductivity of about 40-41 mS/cm; and/or
   iii. eluting the oligo-PEGylated protein from the first HIC material is carried out by linear gradient from about 54-55 mS/cm to about 1-5 mS.cm
      and wherein optionally the protein is EPO.

12. The process according to claim 1, wherein the process is carried out using a mixture of buffer A and buffer B, wherein buffer A comprises 25 mM HEPES, pH 7.5, 500 mM $Na_2SO_4$, and wherein buffer B comprises 25 mM HEPES, pH 7.5, and wherein
   i. the two stage HIC conditions are at about 13.5% buffer B; and/or
   ii. eluting the mono-PEGylated protein from the second HIC material is at about 40% buffer B; and/or
   iii. eluting the oligo-PEGylated protein from the first HIC material is carried out by linear gradient from about 13.5% to about 80% buffer B
   and wherein optionally the protein is EPO.

13. The process according to claim 1, wherein elution of the mono-PEGylated protein from the second HIC material comprises a step elution, optionally followed by a gradient elution.

14. The process according to claim 1, wherein the mono-PEGylated protein composition comprises at least about 99% mono-PEGylated protein.

15. The process according to claim 1, wherein the protein mixture comprises at least 10% oligo-PEGylated protein.

16. The process according to claim 1, wherein mono-PEGylated protein comprises a PEG residue having a molecular weight of at least about 20 kDa.

17. The process according to claim 1, wherein the mono-PEGylated protein composition is a pharmaceutical composition, the process further comprising formulating the second HIC eluate with a pharmaceutical excipient.

\* \* \* \* \*

SEQUENCE LISTING

<160> NUMBER OF SEQ ID NOS: 2

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 166
<212> TYPE: PRT
<213> ORGANISM: Homo sapiens

```
<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65              70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```